(12) United States Patent
LaViola et al.

(10) Patent No.: US 12,293,851 B2
(45) Date of Patent: May 6, 2025

(54) IRRADIATION DEVICES, SYSTEMS AND METHODS

(71) Applicant: Precision X-Ray, Inc., Madison, CT (US)

(72) Inventors: John LaViola, Orange, CT (US); William McLaughlin, Guilford, CT (US); William Reeves, Guilford, CT (US); Robert Conley, Lebanon, CT (US); Michael Piombino, West Haven, CT (US)

(73) Assignee: Precision X-Ray, Inc., Madison, CT (US)

( * ) Notice: Subject to any disclaimer, the term of this patent is extended or adjusted under 35 U.S.C. 154(b) by 328 days.

(21) Appl. No.: 17/881,416

(22) Filed: Aug. 4, 2022

(65) Prior Publication Data

US 2023/0352204 A1 Nov. 2, 2023

Related U.S. Application Data

(60) Provisional application No. 63/337,453, filed on May 2, 2022.

(51) Int. Cl.
*G21K 5/08* (2006.01)
*A61L 2/08* (2006.01)
*A61L 2/26* (2006.01)

(52) U.S. Cl.
CPC ............... *G21K 5/08* (2013.01); *A61L 2/082* (2013.01); *A61L 2/26* (2013.01); *A61L 2202/11* (2013.01)

(58) Field of Classification Search
CPC . A61L 2/08; A61L 2/081; A61L 2/082; A61L 2/084; A61L 2/085; A61L 2/087; A61L 2/088; A61L 2/10; A61L 2/12
See application file for complete search history.

(56) References Cited

U.S. PATENT DOCUMENTS

| 2,416,142 A | 2/1947 | Bennett |
| 7,682,641 B1 * | 3/2010 | Vasilenko ............ A23L 3/26 426/237 |

(Continued)

FOREIGN PATENT DOCUMENTS

| EP | 2412388 A1 | 2/2012 |
| WO | 2022/087357 A1 | 4/2022 |

*Primary Examiner* — Dani Fox
*Assistant Examiner* — Miya Downing
(74) *Attorney, Agent, or Firm* — Verrill Dana, LLP

(57) ABSTRACT

The invention provides an irradiation system, devices, and methods. The irradiation system includes a shielded housing; at least one canister disposed within the shielded housing, the at least one canister containing a material for irradiation within an interior volume of the at least one canister; wherein the at least one canister has a body disposed between a first end cap disposed at a first end of the canister and a second end cap disposed at a second end of the canister opposed to the first end; an ionizing radiation source disposed within the shielded housing adapted for emitting an ionizing radiation having at least one selected incident irradiation field geometry directed generally at the body of the at least one canister; wherein at least one canister is disposed on a rotating mechanism for rotating the at least one canister about a central horizontal or longitudinal axis extending from an isocenter of the first end cap to an isocenter of the second end cap for increasing uniform distribution of radiation of the material contained within the canister.

30 Claims, 21 Drawing Sheets

(56) References Cited

U.S. PATENT DOCUMENTS

| | | |
|---|---|---|
| 11,583,602 B2 * | 2/2023 | Cawley .................... A61L 2/26 |
| 2008/0273661 A1 | 11/2008 | Kirk |
| 2012/0152885 A1 | 6/2012 | Munoz |
| 2017/0118829 A1 | 4/2017 | Hartman et al. |

* cited by examiner

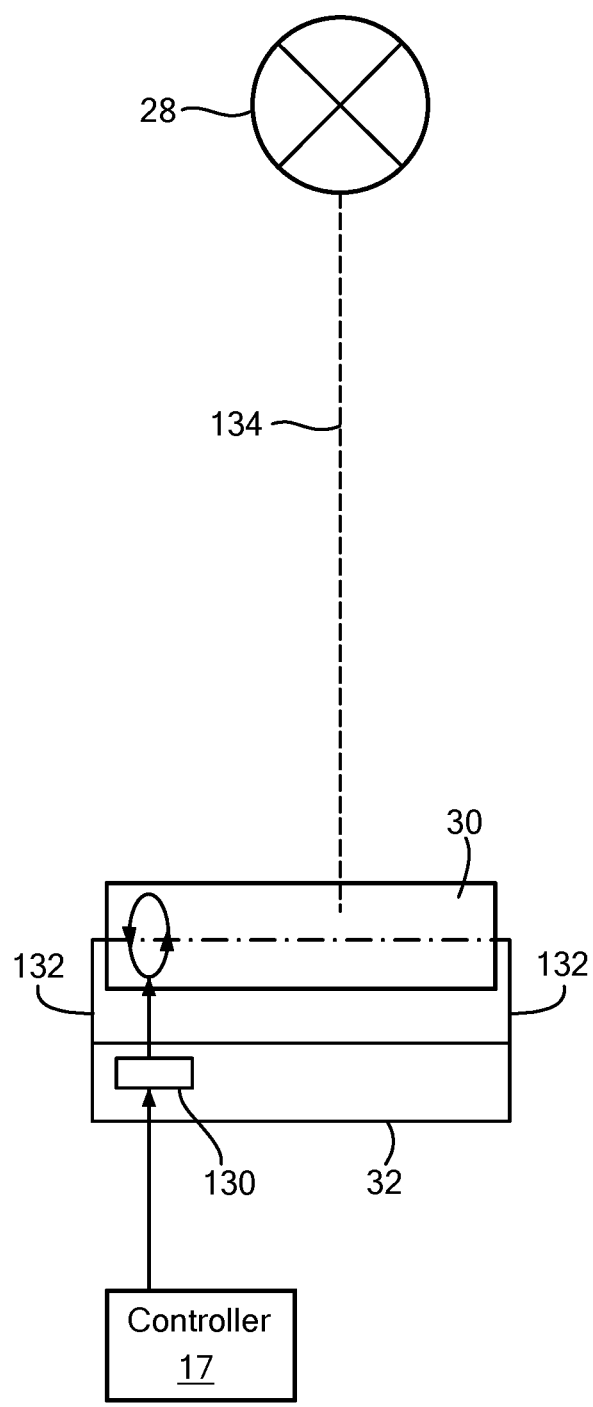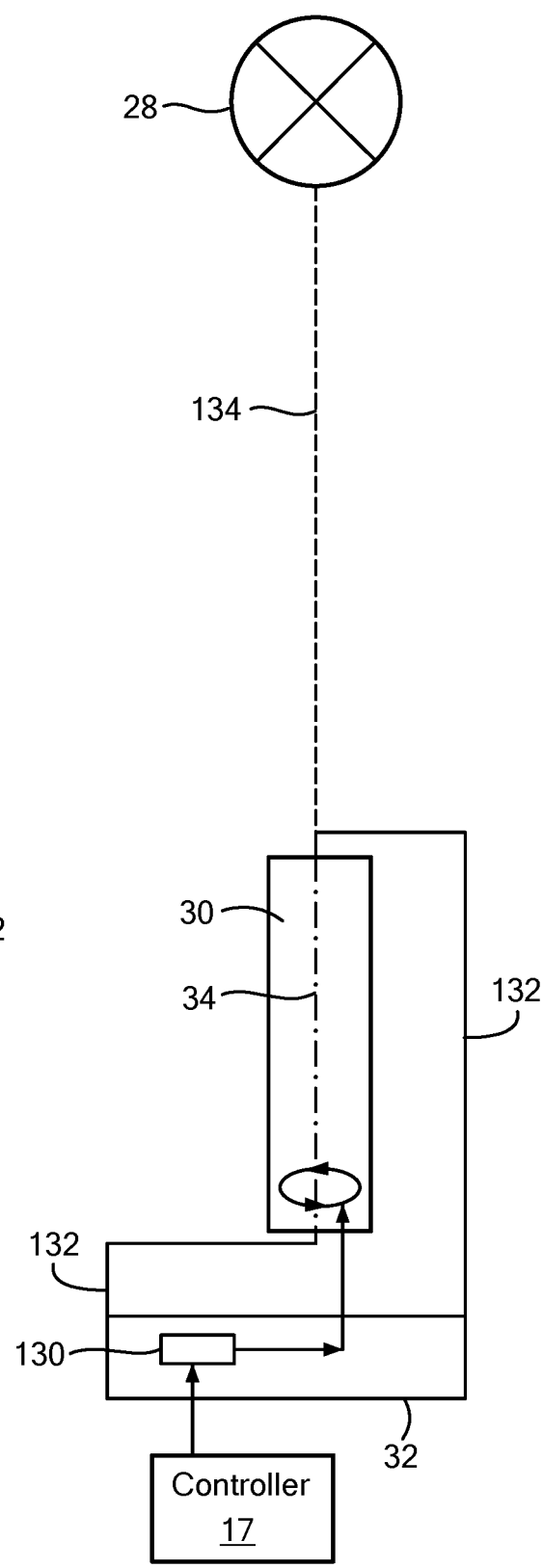
*FIG. 9A*
*FIG. 9B*

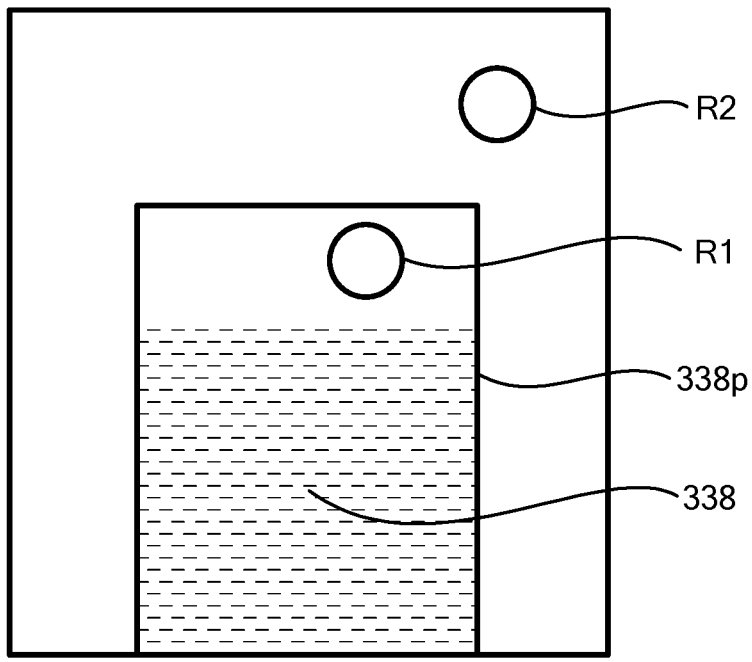

FIG. 17C

```
┌─────────────────────────────────────────────────────────────┐
│ Identifying a first region R1 of an image of the irradiation │
│ volume corresponding to a region in which the radiation      │
│ which has passed through packaging without passing           │
│ through the sample is detected                               │
│                           202a                               │
└─────────────────────────────────────────────────────────────┘
                              ↓
┌─────────────────────────────────────────────────────────────┐
│ Identifying a second region R2 of the image of the irradiation│
│ volume corresponding to a region in which radiation which    │
│ has passed directly to the detector is detecting without     │
│ passing through the package and the sample                   │
│                           202b                               │
└─────────────────────────────────────────────────────────────┘
                              ↓
┌─────────────────────────────────────────────────────────────┐
│ Comparing image data of the first region R1 and the second   │
│ region R2 to estimate an amount of radiation absorbed by     │
│ packaging                                                    │
│                           202c                               │
└─────────────────────────────────────────────────────────────┘
                              ↓
┌─────────────────────────────────────────────────────────────┐
│ Determining an optimum irradiation data plan including       │
│ compensating for radiation absorbed by packaging             │
│                           204a                               │
└─────────────────────────────────────────────────────────────┘
```

FIG. 17D

IRRADIATION DEVICES, SYSTEMS AND METHODS

STATEMENT REGARDING FEDERALLY SPONSORED RESEARCH OR DEVELOPMENT

Not Applicable.

BACKGROUND OF THE INVENTION

This section is intended to provide a background or context. The description may include concepts that may be pursued but have not necessarily been previously conceived or pursued. Unless indicated otherwise, what is described in this section is not deemed prior art to the description and claims and is not admitted being prior art by inclusion in this section.

Plant based materials such as, for a non-limiting example, cannabis are susceptible to contaminants. Whether grown indoors or outdoors, and particularly in a humid environment, a cannabis plant's characteristics including a closed bud leave the plant susceptible to a host of microbial pathogens. It is estimated that, on average, 10-15% of cannabis product fails post-harvest microbial contamination testing. As cannabis sales increase, the percentage of product which fails post-harvest testing can be expected to increase. When the cannabis product fails testing, the cultivator has limited options including: cleaning and retesting the product, transferring the product to another facility for cleaning and retesting, remediating the product in preparation for processing including removal of active and selected inactive ingredients for extract manufacture, and/or destroying the product. Thus there is a need for improved post-harvest microbial treatment in cannabis production.

The treatment of objects and bulk materials using radiation, such as X-rays, can be an effective method of treating a variety of objects or materials such as plant-based materials, herbs, seeds, cannabis, marihuana (also called marijuana) including dried flowers, leaves, stems and seeds of the cannabis plant, food stuffs, tobacco, stem cells, blood, and medical devices. Radiation can also be used with animals and insects. Some useful effects of irradiation are to: destroy or degrade pathogens (e.g. virus, bacteria, mold) or leucocytes; destroy unwanted insects and chemical materials such as pesticides; and delay biological processes such as the ripening of fruit.

The irradiation process for a given application requires a specific uniformity of the distribution of absorbed dose throughout the object being irradiated. A 10% variation of deposited dose throughout the object is typically acceptable, although the acceptable variation changes depending on the application.

Isotopic sources such as Caesium-137 (Cs-137) and Cobalt-60 (Co-60) are commonly used for irradiation. These isotopic sources emit gamma photons with energies of 662 keV and 1.2 MeV respectively. The relatively high energy photons penetrate well through organic materials such as food stuffs and therefore easily achieve a good dose distribution. However, these isotropic sources have undesirable alternative uses and require large fixed facilities with significant radiation shielding and security.

X-ray sources can be used for irradiation and have been a trusted source in the medical, agricultural and food industries for over 75 years. An X-ray source is typically an evacuated sealed tube in which electrons emitted from a tungsten filament (the cathode) are accelerated onto a metal sample (the anode) through the use of electrical voltage. Isotopic sources emit a single wavelength of radiation. In an X-ray source, the anode material re-emits the energy received from the electrons as characteristic X-ray emission lines lying on top of Bremsstrahlung radiation spectrum extending from very low energy X-ray photons up to the voltage potential applied between anode and cathode. Because X-ray sources generate this broad Bremsstrahlung spectrum of radiation, the uniformity of absorbed dose they generate is inferior to isotopic sources of the same maximum energy when used for irradiation.

X-ray sources have an advantage of only producing radiation when they are energized, so they present less of a radiological security risk and can be used in mobile systems. The power dissipation of these devices and hence their X-ray output is low. X-ray sources also have lower energy, typically 25 kV to 550 kV, than Cs-137 and Co-60 which can lead to inferior dose uniformity.

It is an aim of the present invention to address at least one disadvantage associated with the prior art.

BRIEF SUMMARY OF THE INVENTION

The below summary is merely representative and non-limiting. At least one of the above problems is overcome, and other advantages may be realized, by the use of the embodiments of the invention.

The present invention features a deep cleaning ionizing radiation technology such as X-ray technology for providing anti-microbial decontamination for a material, product or sample, including plant-based materials or product.

An advantage of at least one example or embodiment of the invention is that for a particular product material or sample for irradiation, the irradiation intensity and quantity of product material is optimized to achieve the desired irradiation and decontamination of the maximum quantity of product material in the shortest amount of time. In use, the system and devices are configured and the methods are provided for a more uniform radiation dose of the irradiated material, together with simplified methods and devices for providing system and device feedback for easy and real time selection, monitoring, modification, adjustment and fine tuning, and modulation, control and optimization of the operating parameters of the system including for non-limiting examples, the radiation dose, rate, duration, and output by the radiation source.

In an aspect, the invention features an irradiation system comprising: a shielded housing; at least one canister disposed within the shielded housing, the at least one canister containing a material for irradiation within an interior volume of the at least one canister; wherein the at least one canister has a body disposed between a first end cap disposed at a first end of the canister and a second end cap disposed at a second end of the canister opposed to the first end; an ionizing radiation source disposed within the shielded housing adapted for emitting an ionizing radiation having at least one selected incident irradiation field geometry directed generally at the body of the at least one canister; wherein the at least one canister is disposed on a rotating mechanism for rotating the at least one canister about a central horizontal or longitudinal axis extending from an isocenter of the first end cap to an isocenter of the second end cap for increasing uniform distribution of radiation of the material contained within the canister.

In an embodiment, the invention features an irradiation system wherein at least one of the first end cap and the second end cap is configured for selectively sealing and unsealing at least a portion of a corresponding end of the canister.

In an embodiment, the invention features an irradiation system wherein at least one of the first end cap and the second end cap has at least one port configured for fluidically connecting an exterior of the canister to the interior volume of the canister.

In an embodiment, the invention features an irradiation system wherein the irradiation system comprises at least one channel tube having dimensions for insertion into the at least one port for fluidically connecting the exterior of the canister to the interior volume of the canister.

In an embodiment, the invention features an irradiation system wherein at least one of the at least one port and the at least one channel tube is configured such that at least one of the at least one port and the at least one channel tube are selectively sealed and unsealed.

In an embodiment, the invention features an irradiation system wherein the rotating mechanism is modulated or adjusted in a manner selected from the group consisting of a continuous manner, a non-continuous manner and a combination of each of the aforementioned.

In an embodiment, the invention features an irradiation system wherein at least one of the ionizing radiation source and the rotating mechanism is controlled based on a control technology selected from the group consisting of an imaging control technology, an optical control technology, an electromagnetic closed-loop control technology, an electromagnetic semi-closed loop control technology, and at least two of the aforementioned control technologies.

In an embodiment, the invention features an irradiation system further comprising: a control technology including an imaging control technology having at least one radiation detector for measuring at least one of a density and a distribution of the material during irradiation based on one or more projection images through the material; wherein the rotating mechanism is configured with at least one clearance portion for the at least one radiation detector.

In an embodiment, the invention features an irradiation system wherein at least one of the first end cap and the second end cap includes a component which is configured for selective extension and contraction for selectively constraining geometrically within the canister at least one of the material for irradiation and a containment device containing the material for irradiation.

In an embodiment, the invention features an irradiation system wherein at least one of the first end cap and the second end cap includes a component which is configured for selectively constraining geometrically within the canister at least one of the material for irradiation and a containment device containing the material for irradiation within the canister for optimizing alignment to at least one selected incident irradiation field geometry.

In an embodiment, the invention features an irradiation system wherein at least one of the first end cap and the second end cap includes a component which is configured for selectively constraining geometrically at least one of the material for irradiation and a containment device containing the material for irradiation within the canister for minimizing movement during rotation of the canister of the at least one of the material for irradiation and the containment device containing the material for irradiation.

In an embodiment, the invention features an irradiation system wherein the ionizing radiation source consists of one ionizing radiation source.

In an embodiment, the invention features an irradiation system further comprising on a programmable shelf on which the rotating mechanism is disposed; wherein the programmable shelf is selectively positioned with respect to the ionizing radiation source for achieving the at least one selected incident irradiation field geometry directed generally at the body of the at least one canister.

In an embodiment, the invention features an irradiation system further comprising a probe configured for selected insertion of a first end of the probe to a selected position within the interior volume of the canister via at least one of the at least one port and the at least one channel tube and for selected retraction therefrom; wherein the probe is configured for measurement of a property including at least one of a temperature level, a humidity level, and a radiation level.

In an embodiment, the invention features an irradiation system further comprising a controller configured with a capability to integrate information received from at least one of a control technology and a probe configured for insertion into the interior volume of the canister for optimization of the irradiation system with respect to controlling at least one of: at least one operating parameter of the source of ionizing radiation, at least one operating parameter for at least one component configured for selectively constraining geometrically within the canister at least one of the material and a containment device containing the material, at least one operating parameter of the rotating mechanism, and at least one operating parameter for selective positioning of a programmable shelf on which the rotating mechanism is disposed; wherein optimization of the irradiation system includes maximizing uniform distribution of radiation of the material within the canister.

In an embodiment, the invention features an irradiation system further comprising a controller; wherein the controller is configured with a capability for acquiring data for at least one selected microbe including a pre-irradiation microbial contamination level for at least one selected microbe on a weight or volume basis and a corresponding weight or volume of the material, and calculating a pre-irradiation microbial contamination level for the at least one selected microbe in the material based on the acquired data; wherein the controller is configured with a capability for acquiring data including an identification of a target jurisdiction and correlating the target jurisdiction with a microbial contamination regulatory standard for the target jurisdiction for the at least one selected microbe; and wherein the controller is configured with a capability for determining an optimum irradiation data plan for an optimization of at least one operating parameter of the source of ionizing radiation based upon a comparison of the pre-irradiation microbial contamination level for at least one selected microbe in the material and the microbial contamination regulatory standard for the target jurisdiction for the at least one selected microbe.

In an embodiment, the invention features an irradiation system wherein the controller is configured with a capability for acquiring data for the at least one selected microbe including the pre-irradiation microbial contamination level for the at least one selected microbe on a weight or volume basis and the corresponding weight or volume of the material based on at least one of manual data input via a user interface integrated with the controller, data input received by the controller via a weighing mechanism integrated with the controller, data input received by the controller via a scanning of a machine readable information code, and a combination of the aforementioned.

In an embodiment, the invention features an irradiation system wherein the at least one operating parameter comprises at least one of: a total radiation dose (gray); a rate of radiation delivery (rem) per unit time (minutes); a total duration of an irradiation (minutes); a radiation output by the source of ionizing radiation; and a beam angle of the source of ionizing radiation upon activation over the duration of the irradiation.

In an embodiment, the invention features an irradiation system wherein at least one of the operating parameters including the rate of radiation delivery, the radiation output and the beam angle comprises a manner of operation of the operating parameter over the total duration of the irradiation selected from group consisting of varying, fixed and a combination of the aforementioned.

In an aspect, the invention features a device for receiving ionizing radiation from an ionizing radiation source comprising: a canister having a body, a first end cap disposed at a first end of the body and a second end cap disposed at a second end of the body opposed to the first end; wherein at least one of the first end cap and the second end cap has a component which is configured for selective extension and contraction for selectively constraining geometrically within the canister at least one of a material for irradiation contained within an interior volume of the canister and a containment device containing the material for irradiation within the interior volume of the canister for optimizing alignment to at least one selected incident irradiation field geometry directed generally at the body of the canister from the ionizing radiation source.

In an aspect, the invention features a method of irradiation of a material comprising: providing an ionizing radiation source within a shielded housing; providing at least one canister disposed on a rotating mechanism within the shielded housing; wherein the at least one canister contains a material for irradiation within an interior volume of the at least one canister; wherein the at least one canister has a body disposed between a first end cap disposed at a first end of the canister and a second end cap disposed at a second end of the canister opposed to the first end; emitting an ionizing radiation having at least one selected incident irradiation field geometry directed generally at the body of the at least one canister from the ionizing radiation source; rotating the at least one canister about a central horizontal or longitudinal axis extending from a first isocenter of the first end cap to a second isocenter of the second end cap for increasing uniform distribution of radiation of the material contained within the canister; and providing a component for selectively constraining geometrically within the canister at least one of the material for irradiation and a containment device containing the material for irradiation for optimizing alignment to a geometry of the beam of radiation incident on the body of the canister.

These and other features, aspects, and advantages of the present invention will become better understood with regard to the following description, claims and appended drawings.

Embodiments of the invention are understood with reference to the appended claims.

Within the scope of this application, it is envisaged that the various aspects, embodiments, examples, and alternatives, and in particular the individual features therefor, described in the proceeding paragraphs, in the claims and/or in the following description and drawings can be taken independently or in any combination. For example, features described in connection with one embodiment are applicable to all embodiments, unless such features are incompatible.

For the avoidance of doubt, it is to be understood that features described with respect to one aspect of the invention can be included within any other aspect of the invention, alone or in appropriate combination with one or more features.

BRIEF DESCRIPTION OF THE SEVERAL VIEWS OF THE DRAWINGS

One or more embodiments of the invention are now described by way of example only with reference to the accompanying figures in which:

FIG. 9A shows a schematic of a rotating mechanism which incorporates a rotating mechanism control technology according to one non-limiting embodiment;

FIG. 9B shows a schematic of a rotating mechanism which incorporates a rotating mechanism control technology according to one non-limiting embodiment;

FIG. 17C illustrates schematically an acquired image of a sample inside packaging including a canister and optional containment device according to a non-limiting embodiment;

FIG. 17D illustrates a further method of operating the irradiation system according to one non-limiting embodiment;

DETAILED DESCRIPTION OF THE INVENTION

Figure 1:
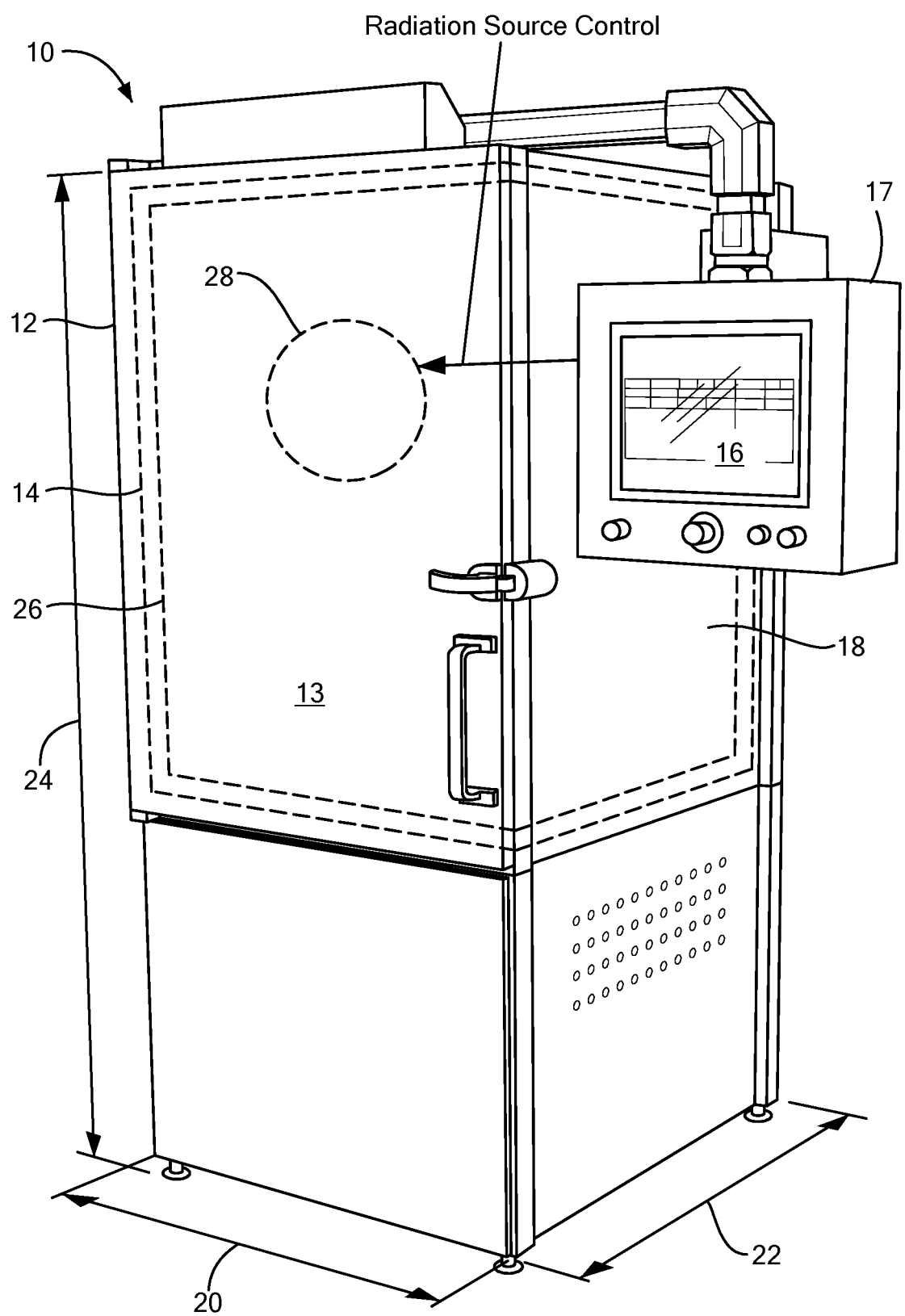
FIG. 1 shows a substantially exterior view of the irradiation system according to one-limiting embodiment.

International Publication Number WO 2022/087357 A1 corresponding to International Application Number PCT/US2021/056177 and International Publication Number WO 2022/087363 A1 corresponding to International Application Number PCT/US2021/056183 are incorporated herein by reference in their entirety.

The present invention features systems, devices and methods for treatment of a material or product or sample. For purposes of this application, the terms "material(s)", "product(s)", "product material(s)" and "sample(s)" unless otherwise particularly specified are used interchangeably and are not limiting. The material for treatment includes plant-based materials or product such as, for non-limiting examples, plant materials, cannabis, and herbs such as peppercorns and/or dried spices, and/or liquid samples. The treatment of the material includes deep cleaning ionizing radiation technology such as X-ray technology for anti-microbial decontamination. The systems, devices and methods of the invention incorporate features for irradiating, measuring, monitoring, modifying and adjusting, fine-tuning, modulating and controlling, and/or optimizing the irradiation of a product material or sample.

Unlike other methods of cleaning which only reach the surface of materials and/or affect the quality of the product material or sample, ionizing radiation such as X-ray radiation penetrates through the product material or sample and in the case of flowering plant materials, penetrates the entire flower, killing both surface and deep-seated endophytic microbes. X-ray technology is a 'cold' treatment process that cleans the respective plant material without heating the flower. Ionizing radiation such as X-ray technology has a 99.9% success rate in killing harmful molds and bacteria, without altering the concentrations of, for example, THC, CBD, cannabinoid or terpene concentrations of the underlying irradiated material. Ionizing radiation such as X-ray technology is proven to be effective in killing contaminants after one irradiation treatment and preventing regrowth against microbials such as, for non-limiting examples, *Aspergillus, Mucor fungi, E. Coli, Salmonella, Listeria* bacteria, *Pseudomonas aeruginosa, Penicillium fungi,* and *Staphylococcus aureus.* The X-ray treatment maintains the look, feel and smell of the plant including the flower of the plant. Uniform dosing penetrates through density material such as for non-limiting examples, flowers, buds, and packed ground material.

The system, devices and methods of the invention incorporate various options for measuring, monitoring, modifying and adjusting, fine-tuning, modulating and controlling, and/or optimizing irradiation taking into account variables such as, for non-limiting examples, the amount of product material; the density or density variation of the material for treatment; the amount of irradiation absorbed by packaging of the material; and movement and/or dislocation of the material during processing.

Reference is now made in detail to various embodiments, examples of which are illustrated in the accompanying drawings.

The systems, devices and methods of the invention are illustrated in FIGS. 1-18.

FIG. 1 shows substantially an exterior view of the irradiation system 10. The irradiation system 10 includes a cabinet 12 including a chamber 14 defining an interior volume. The cabinet 12 includes a shielded housing 26 which prevents or limits the passage of radiation emitted from a radiation source 28 disposed within the chamber 14 of the cabinet 12 to an exterior of the cabinet 12. One side of the cabinet 12 includes an access door or hatch 13 which permits access to the interior of the chamber 14 throughout the shielded housing 26. In a preferred embodiment, the shielded housing 26 is lead. The sealed, lead-lined chamber 14 ensures safety of the personnel during the treatment process.

FIG. 1 shows the shielded housing 26 as an interior lining of chamber 14 and continuous with the walls of the chamber 14. In an alternative non-limiting embodiment, the shielded housing 26 is separate from the walls of the chamber 14 and is surrounded or enclosed by the walls of the chamber 14. In other non-limiting embodiments, the shielded housing 26 surrounds or encloses the chamber 14 and is either continuous with the walls of the chamber 14 as an outer chamber lining or is separate from the walls of chamber 14. In the latter embodiments, the access door or hatch 13 permits access through the shielded housing 26 enclosing the chamber 14 into the interior volume of chamber 14.

In a preferred embodiment, the radiation source 28 is configured to emit or output ionizing radiation such as X-ray radiation. X-ray radiation is described in the following description, but other kinds or radiation such as gamma radiation can be generated or used.

The system includes a controller 17 which controls operation of the radiation source and other components of the irradiation system. The controller 17 is disposed within the system 10 or separate from the system 10. The system 10 or device of the invention includes a user interface such as a touchscreen user interface 16 disposed on the exterior surface 18 or adjacent to or otherwise outside of the cabinet 12. The user interface enables communication with the controller 17 for selecting or varying operating parameters for the radiation source including, for non-limiting examples, radiation dose and time settings, as well as the operating parameters for other system components including for non-limiting examples the canister, the rotating mechanism supporting the canister, and the shelf on which the rotating mechanism is disposed. In non-limiting embodiments of the invention, the user interface 16 and/or the controller 17 of the irradiation system 10 incorporates or integrates manually set parameters, preset parameters, preset programs, and/or a combination of one or more of the aforementioned. In one non-limiting embodiment, the user interface 16 is integrated with a camera, such as a full screen web camera, for interior cabinet 12 viewing including viewing of the product material or sample or the packaging enclosing the product material or sample. In a non-limiting embodiment, the interface 16 and/or controller 17 provide logs for the traceability of the processing cycle. The radiation source includes other elements not shown in these figures such as a power supply.

The width 20, depth 22, and height 24 dimensions of the cabinet 12 of the irradiation system 12 can be varied according to the application. In embodiments of the invention, the width 20 is in a range of 34 inches to 76 inches, preferably in a range of 35 incudes to 57 inches, more preferably in a range of 36 inches to 48 inches; and most preferably is 38 inches; the depth 22 is in a range of 38 inches to 84 inches, and preferably in a range of 39 inches to 63 inches, more preferably in a range of 40 inches to 53 inches; and most preferably is 42 inches; and the height 24 is in a range of 70 inches to 86 inches, and preferably in a range of 74 inches to 82 inches, more preferably in a range of 76 inches to 80 inches and most preferably is 78 inches.

Figure 2:
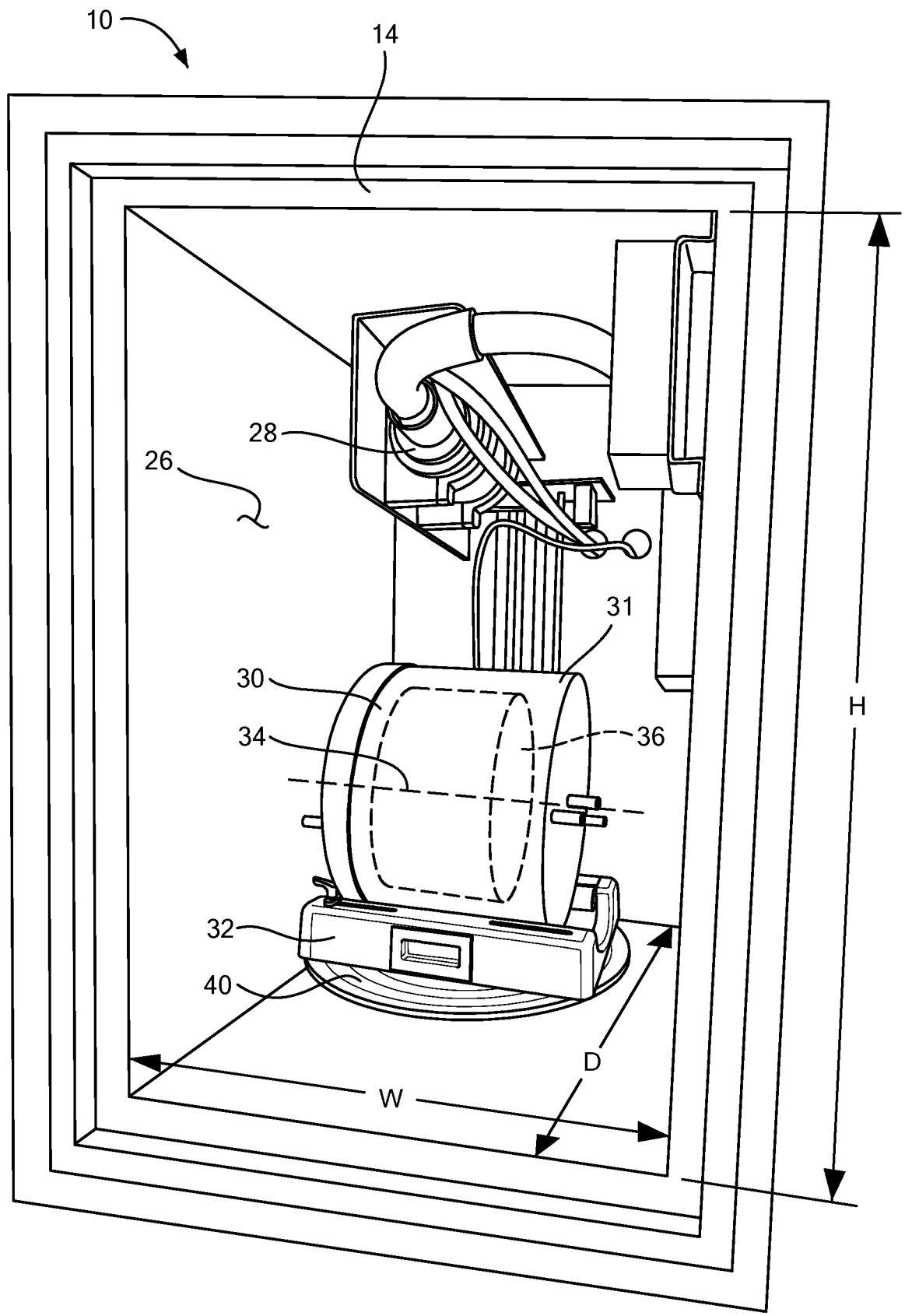
FIG. 2. shows an interior view of the irradiation system according to one non-limiting embodiment.

FIG. 2 is a view of the interior of the radiation shielded cabinet enclosure or housing 26 of the sealed, radiation shielded chamber 14 of the irradiation system 10 shown in FIG. 1. The enclosure or housing 26 includes an irradiation or ionizing radiation source 28 such as an X-ray source or tube (at top) configured for exposing or irradiating at least one canister 30, drum or cylinder having a body 31 enclosed by the shielded cabinet housing 26. The canister 30 is disposed on a rotating stage or auto roll mechanism 32. For purposes of this application, the terms "rotating stage(s)", "auto roll mechanism(s)", "rotating mechanism(s)" and "rotating stage mechanism(s)" are used interchangeably and are not limiting. The rotating mechanism 32 is configured for rotating the canister, drum on cylinder about a central horizontal or longitudinal axis 34 thereby moving the product material 36 or sample contained therein through the beam or field of radiation or irradiation volume emitted from the irradiation or ionizing radiation source 28 and providing dose uniformity throughout the product material 36.

FIG. 2 shows the radiation source 28 disposed above the rotating canister 30. In other non-limiting embodiments, the radiation source is disposed below or at another position relative to the canister 30 as long as the wall or surface 31 of the canister rotates throughout the irradiation volume exposing the product material 36 or sample contained therein substantially to a uniform radiation dose.

The rotating stage or auto roll mechanism 32 is disposed on a shelf which includes preferably a planar shelf or surface 40. The shelf 40 is preferably moveable for repositioning to accommodate one or more differently sized canister(s) 30 and/or different volumes of product material or sample 36 relative to the radiation source 28. In an embodiment, the shelf 40 is programmable for optimization of the position of canister(s) (30) and the product material 36 contained therein in the shielded cabinet housing 26 relative to the radiation source 28.

The ionizing radiation source 28 disposed in the interior of the shielded housing 26 of the cabinet 12 has a kilovoltage peak (kVp) in the range of 30 to 320 kVp and more preferably in a range of 160 to 320 kVp, and most preferably has a 225 kVp maximum. The kilovoltage peak of the irradiation or ionizing radiation source provides for deep penetration of radiation such as X-ray radiation into the product material or sample for irradiation.

In different non-limiting embodiments, the product material or sample includes loose material, ground material, and/or packed material. The material is contained within a canister or drum or within a containment device enclosed by a canister or drum. In different embodiments, the product material or sample includes dense material such as, for non-limiting examples, flowers, including large, dense buds. In still other non-limiting embodiments, the samples include liquid samples.

The width, depth and height dimensions of the chamber 14 of the cabinet 12 of the irradiation system 10 can be varied according to the application. In embodiments of the invention, the width W is in a range of 27 inches to 60 inches, preferably in a range of 28 incudes to 45 inches, more preferably in a range of 29 inches to 38 inches; and most preferably is 30 inches; the depth D is in a range of 31 inches to 69 inches, and preferably in a range of 33 inches to 52 inches, more preferably in a range of 34 inches to 43 inches; and most preferably is 34.5 inches; and the height H is in a range of 37 inches to 45 inches, and preferably in a range of 39 inches to 43 inches, more preferably in a range of 40 inches to 42 inches and most preferably is 41 inches, as shown in FIG. 2.

The irradiation system 10 includes one or more canisters, drums, and/or cylinders 30 having a body 31 and containing material 36 or sample for irradiation. For purposes of this application, the terms "canister(s)", "drum(s)" and "cylinders(s)" are used interchangeably and are not limiting. Each canister varies in length and diameter depending upon the application and/or the size of the cabinet enclosure and the particular irradiation or ionizing radiation source. In typical embodiments, a canister has a diameter in a range of 4 in. to 24 in., and preferably in a range of 8 in. to 20 in. and more preferably in a range of 12 in. to 16 in., and most preferably a diameter of 14 in. In typical embodiments, a canister has a length in a range of 4 in. to 32 in., preferably a range of 8 in. to 28 in., more preferably in a range of 10 in. to 26 in. and most preferably in a range of 12 in. to 24 in.

Figure 3A:
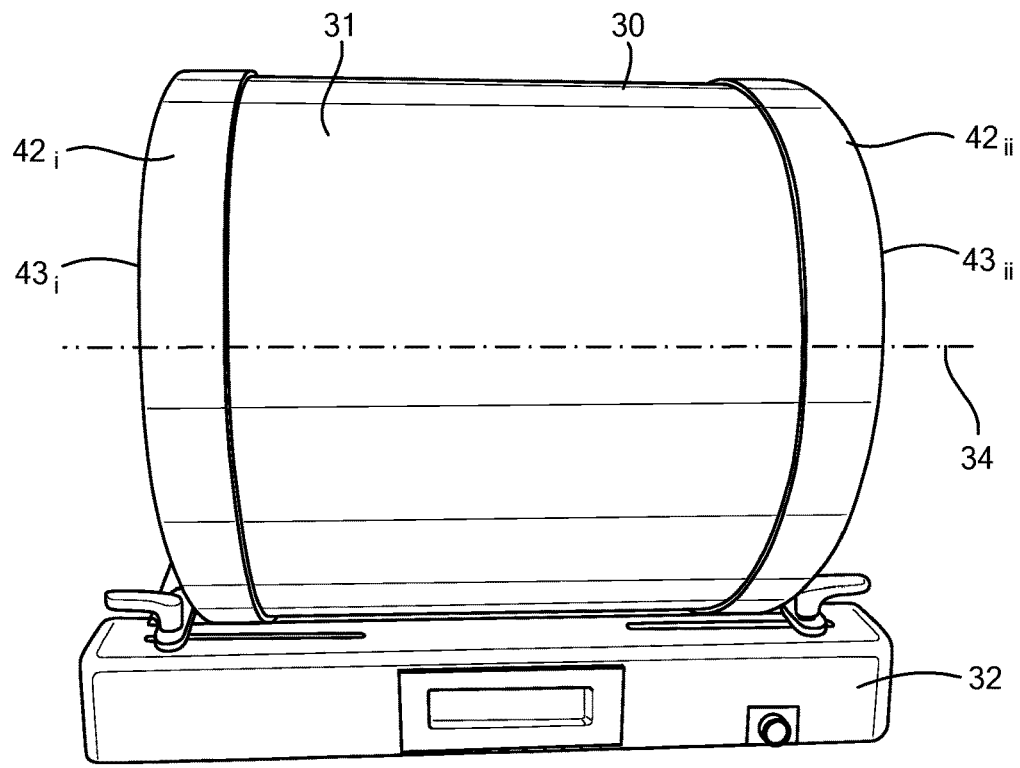
FIG. 3A shows a side view of a canister disposed on a rotating mechanism according to one non-limiting embodiment.
Figure 3B:
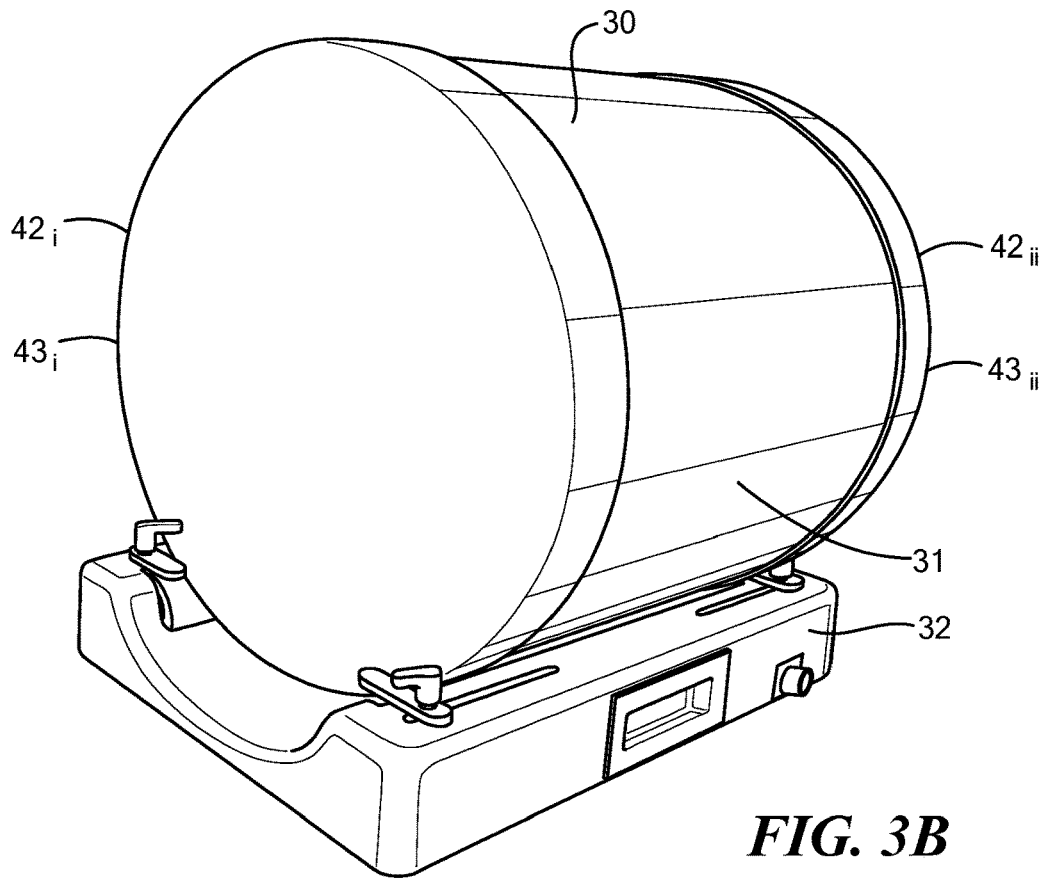
FIG. 3B shows a perspective end view of a canister disposed on a rotating mechanism according to one non-limiting embodiment.

FIG. 3A shows a side view and FIG. 3B a perspective view of an individual canister 30 having a body 31 and an endcaps 42i and 42ii disposed on respective opposing ends 43i and 43ii of the body 31 according to a non-limiting embodiment of the invention. The canister including the canister body and end caps is configured for enclosing an interior volume containing a product material for irradiation. Said product material is optionally contained within a containment device which is then inserted into the interior volume of the canister. In a preferred non-limiting embodiment, at least a portion of at least one end cap is configured for selectively sealing and unsealing at least a portion of a corresponding opposing end of the canister. Such a reversibly sealable end cap or reversibly sealable portion thereof facilitates filling and removal of the product material respectively into and from the interior volume of the canister. In a non-limiting embodiment, at least a portion of at least one end cap is configured for selective removal from and attachment to at least a corresponding portion of a corresponding opposing end of the canister. In another non-limiting embodiment, at least one end cap includes a panel. When the panel is disposed in an open or unsealed position, at least a portion of the corresponding opposing end of the canister is unsealed. When the panel is disposed in a closed or sealed position, at least a portion of the corresponding opposing end of the canister is sealed. In another non-limiting embodiment, at least one end cap includes an opposing end closure which is fixed and is not configured for sealing and unsealing a portion of the corresponding opposing end of the canister. An opposing end closure is shown by element 61 in the non-limiting embodiment shown in FIG. 7.

The canister is disposed on a rotating mechanism 32. The rotating mechanism 32 rotates the canister about a central axis 34 in a selected clockwise or counterclockwise direction. The rotating mechanism 32 includes a motor (not shown) for driving the rotation and orienting the position of the rotating canister relative to the radiation source. The rotation speed and orientation of the rotating canister relative to the radiation source is selectively programmable, variable and controllable. Each canister is fabricated from a canister fabrication material which has a low attenuation to X-rays, such as, for non-limiting examples, carbon fiber, paper and low-density plastics including for non-limiting examples ethylene vinyl acetate, low density polyethylene and polypropylene. In non-limiting embodiments, the canister includes a low-density plastic having a maximum density of 1.2 g/cm$^3$, preferably a maximum density of 1.1 g/cm$^3$ and more preferably a maximum density of 1.0 g/cm$^3$.

Figure 4:
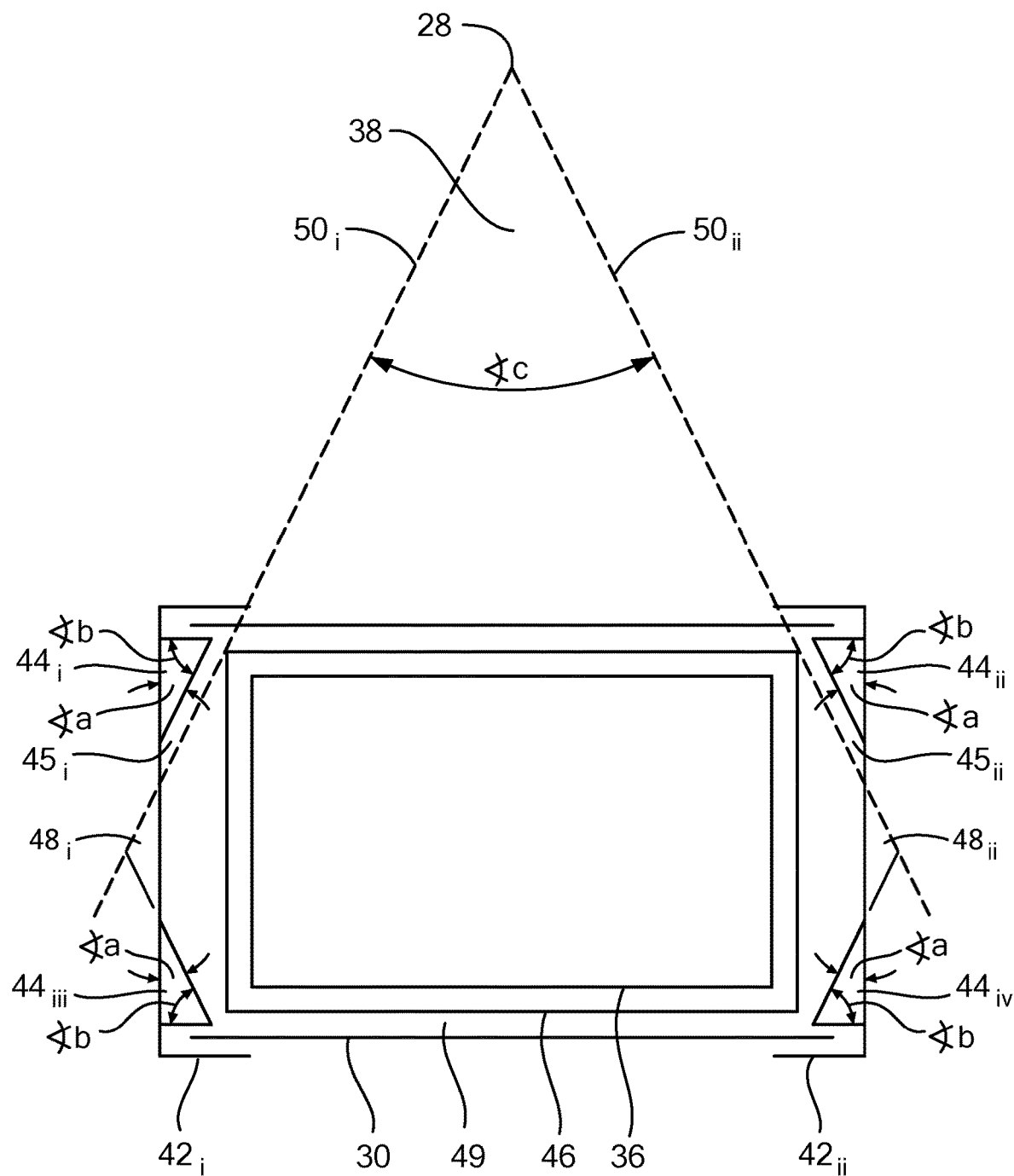
FIG. 4 shows a side cut away view of a canister disposed in a field of a radiation beam emitted from a radiation source according to one non-limiting embodiment.

FIG. 4 shows schematic of a canister 30 or drum having end cap(s) 42*i* and 42*ii*. The end caps include respective component(s) 44*i* and 44*iii* and 44*ii* and 44*iv* each configured for securely holding the irradiated product material 36 or sample in the field of the radiation beam or irradiation volume 38 being emitted or projected from the radiation source 28, such as an X ray source, throughout the rotation of the irradiation treatment process. In the non-limiting embodiment of the invention shown in FIG. 4, the securing components 44*i* and 44*iii* are disposed on the end cap 42*i*, and the securing component 44*ii* and 44*iv* are disposed on the end cap 42*ii* of the canister 30. In a preferred embodiment, the canister includes at least one end cap including one or more securing components. In a more preferred embodiment, the canister includes each of two end caps including one or more securing components. The securing components' secure containment of the irradiated material 36 in the canister 30 throughout the treatment process minimizes damage, breakage or crumbling of the irradiated material 36 and minimizes the need for manual manipulation of the product material 36 as part of the processing treatment.

In a non-limiting embodiment, the product material 36 for irradiation is inserted directly into the canister 30 or drum. In alternative non-limiting embodiments, the product material 36 for irradiation is inserted into one or more containment device(s) 46 which are then placed within the respective canister 30 or drum. The securing components 44*ii*, 44*iii*, 44*ii*, and 44*iv* similarly secure a containment device 46 throughout rotation during the irradiation treatment securely thereby holding the irradiated product material 36 or sample in the field of the radiation beam or irradiation volume 38 and minimizing damage, breakage or crumbling of the irradiated material 36. The containment device includes a bag and/or is fabricated from a material which has a low attenuation to X-rays, such as, for a non-limiting example, carbon fiber.

With respect to beam 38 having an angle c, and the radiation source oriented to emit a beam of radiation toward the canister, the securing components 44*i* and 44*ii* are also configured having a respective angle a and an angle b for restricting movement of the product material 36 or sample from being displaced into a respective "cold" zone 45*i* and 45*ii* where no irradiation is received because of the irradiation geometries. In X-ray technology, the intensity of X-rays shown by 50*i* vary in intensity as compared to the X-rays shown by 50 *ii* because of the variation of the intensity of X-rays emitted by the anode depending on the direction of emission along the anode-cathode axis. This effect is known as the anode heel effect or the heel effect. The securing components are thus also configured for selective optimization of the irradiation intensity projected onto the product material in view of the anode heel effect.

In non-limiting embodiments, dimensional depth components are disposed on one or two end caps. FIG. 4 shows end caps 42*i* and 42*ii* including respective dimensional depth components 48*i* and 48*ii* in a non-limiting embodiment. The dimensional depth components 48*i* and 48*ii* are configured for selective expansion/extension or contraction and thus for selectively increasing or decreasing the interior volume 49 of the canister 30. The dimensional depth components are used to selectively adjust the volume of the canister that falls within the irradiation volume 38. Components 48*i* and 48*ii* are thus configured for selective containment of product material 36 or sample in the irradiation volume 38 thereby optimizing the canister interior volume 49 available for holding product material 36 in the irradiation volume 38. The dimensional depth components are configured for selective symmetrical containment of the product material for irradiation and coincidental to the geometry about the isocenter or offset relative to the isocenter of each end cap. In a preferred embodiment, the canister includes at least one end cap including the dimensional depth component. In a more preferred embodiment, the canister includes each of two end caps including a dimensional depth component.

Thus, one or both end cap(s) 42 of the canister 30, drum or other packaging include components are configured to ensure that the material or sample contained therein for irradiation is constrained geometrically to assure efficacy and optimization of treatment and alignment to the incident irradiation field geometry. FIG. 4 shows a radiation source 28 such as an X-ray tube projecting or directing a field or volume of irradiation 38 towards the canister 30 undergoing irradiation treatment. FIG. 4 shows the radiation source 28 projecting or directing an ionizing radiation beam defined by 50*i* and 50*ii* including a cone-shaped beam having an angle c. In non-limiting embodiments, the irradiation field geometry is selected from geometries consisting of a cone shape, a fan shape, a rectangular cross-section, and other specific geometries known to those of ordinary skill in the art.

Figure 5A:
FIG. 5A shows side view of a canister end cap according to one non-limiting embodiment.
Figure 5C:
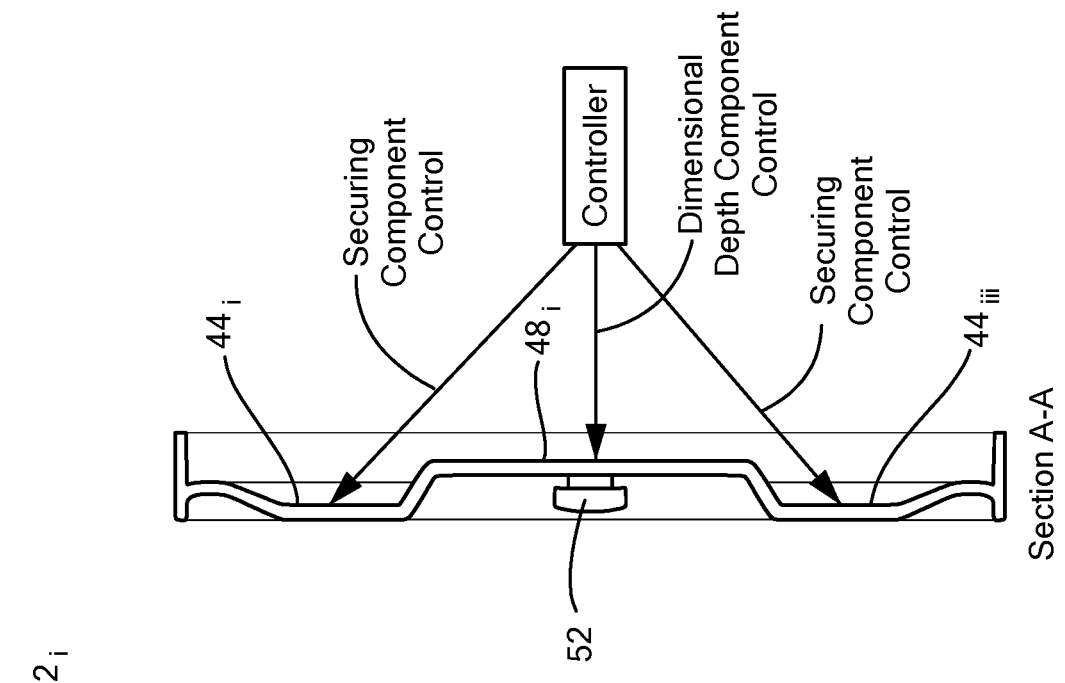
FIG. 5C shows a sectional view of a canister end cap accordingly to one non-limiting embodiment.
Figure 5B:
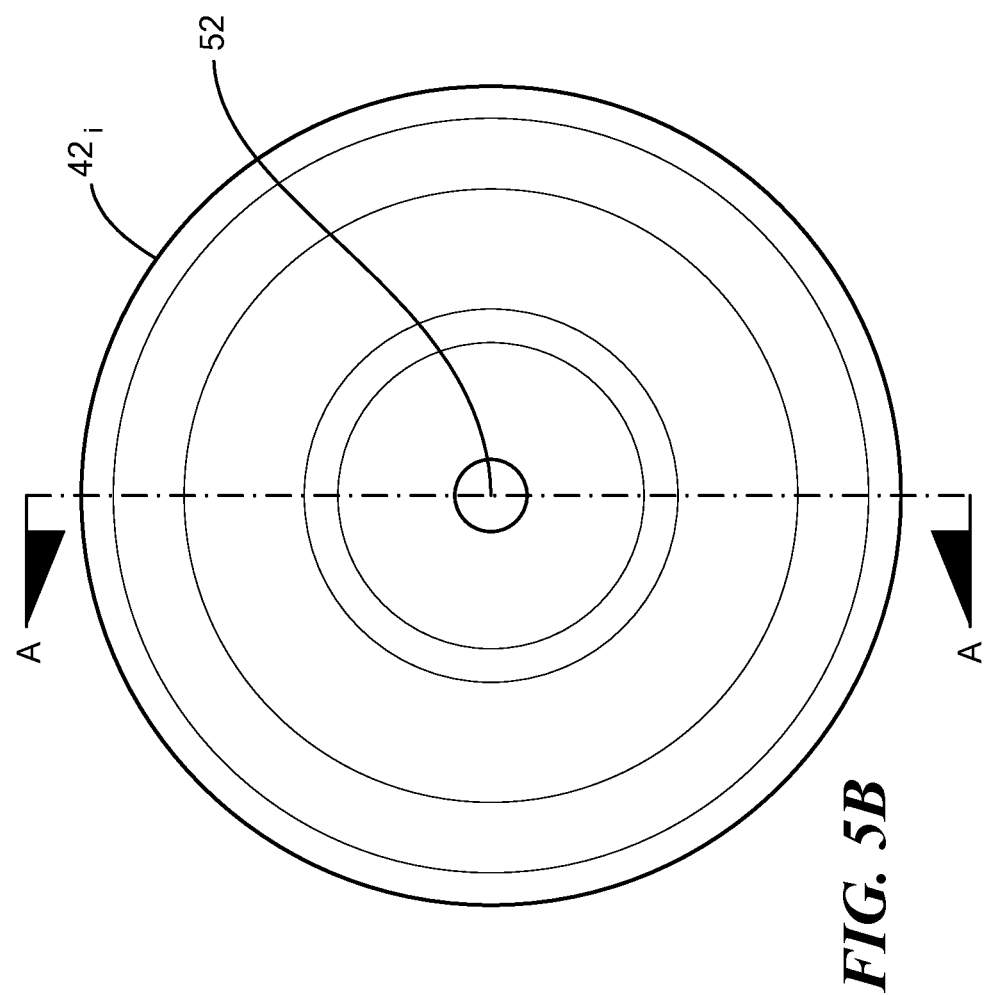
FIG. 5B shows top view of a canister end cap according to one non-limiting embodiment.

FIGS. 5A-5C show different views of an end cap including both securing and dimensional depth components according to a non-limiting embodiment. FIG. 5A shows a side view of an end cap 42*i*. FIG. 5B shows a top view of the end cap 42*i* having a knob 52 disposed at the isocenter of the end cap 42*i*. FIG. 5C shows a sectional view of the end cap 42*i*. The end cap 42*i* is configured with securing components 44*i* and 44*iii* and dimensional depth component 48*i*. Each securing component is configured for containment of the product material disposed in a canister when the end cap 42*i* is disposed on a corresponding opposing end of the canister. The dimensional depth component 48*i* is shown in a recessed position reducing the available interior volume of the canister. Each of the securing and/or dimensional depth components are configured having an accordion-like shape which can be folded/moved toward or folded/moved away from the interior volume of the respective canister 30 thereby optimizing the interior volume of canister 30 which falls within the irradiation volume 38.

In non-limiting embodiments, the one or more of the securing components and/or one or more of the dimensional depth components are flexible, moveable and therefore selectively expandable/extensible and contractible. In non-limiting embodiments, the features of the one or two securing components and a dimensional depth component are incorporated into a collar of the respective end cap. In preferred embodiments, the one or more securing components and/or one or more dimensional depth components incorporate control technology for integrated control of the one or more of the securing components and/or one or more of the dimensional depth components by the controller for adjustment, modification, and/or optimization of the components for optimal positioning of the product material or sample in consideration of the irradiation field geometry.

Figure 6:
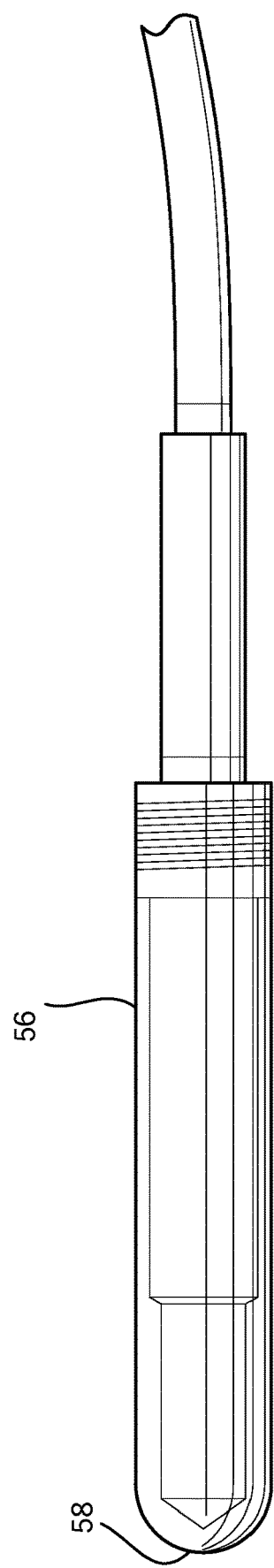
FIG. 6 shows a measurement instrument including a dosimeter probe according to one non-limiting embodiment.

FIG. 6 shows a non-limiting example of an instrument 56 such as a measurement instrument including a dosimeter probe having a first end 58. Non-limiting examples of measurement instruments used with the invention include a radiation dosimeter, a temperature probe, and/or a humidity probe. Such instruments are used to measure properties of the product material or sample for optimization of the system. For a non-limiting example, X-rays which travel in straight lines will either travel through materials such as non-metal materials with a varying degree of attenuation or will be scattered or absorbed by certain materials such as metal materials. The amount of radiation that is received at a dosimeter is indicative of the properties of the sample such as material density and type and can be used to optimize the radiation dosing of the material through for non-limiting examples selected variation of output power and beam width.

In a non-limiting embodiment, the radiation source 28 includes a beam controlling device or collimator which is integrated with the controller for control including selective variation of a size and/or shape of an opening or aperture. The beam controlling device controls the shape and/or width of a beam of radiation emitted by the radiation source 28 towards the irradiation volume 38. Responsive to the controller, the collimator is configured with the capability to selectively shape the irradiation field or volume with a fixed width and shape, a variable width and shape, and a combination of a fixed and variable width and shape over time and/or in response to data input.

Figure 7:
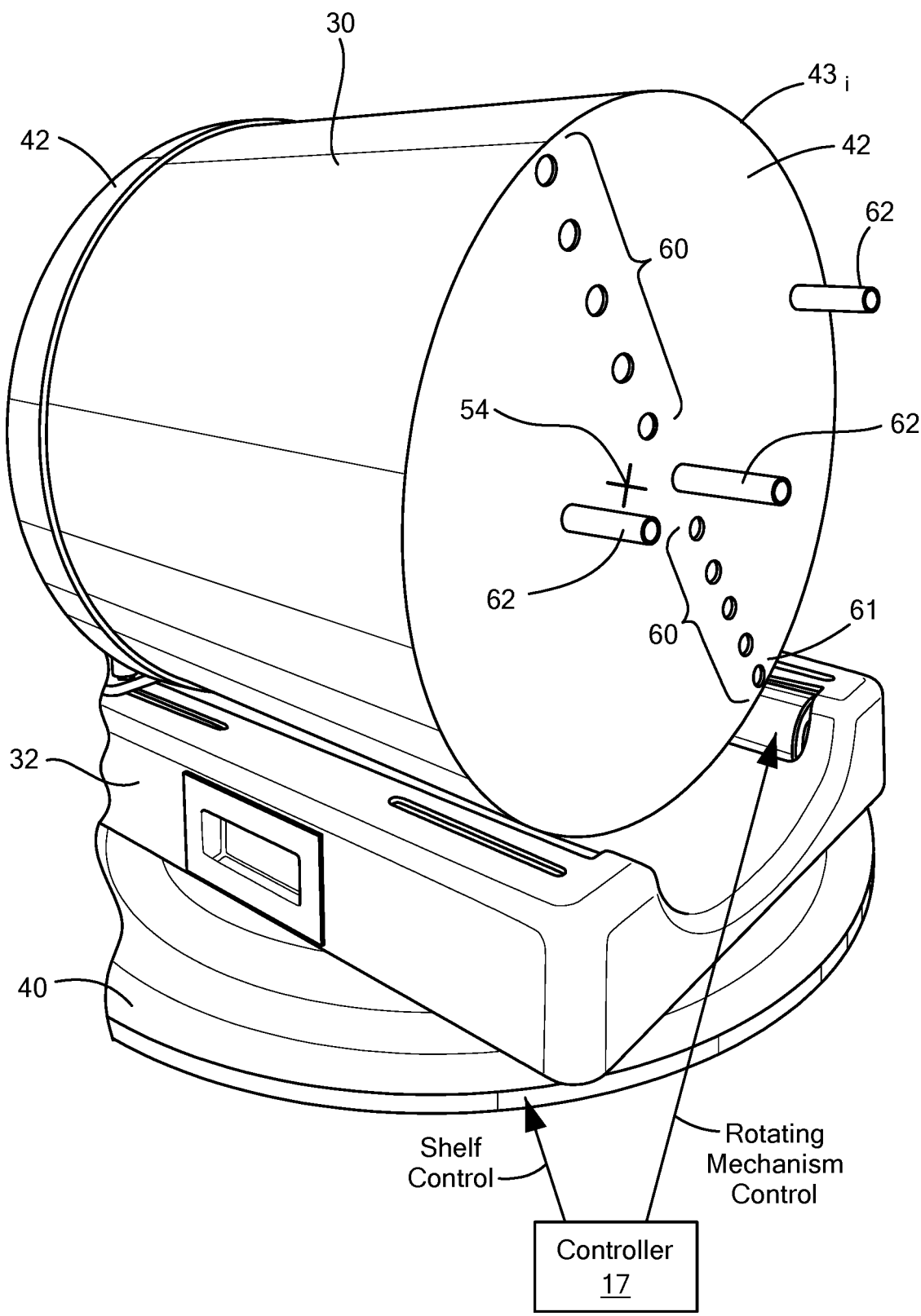
FIG. 7 shows a canister for containment of material for irradiation including an opposing end closure of the canister including ports and channel tubes according to one non-limiting embodiment.

FIG. 7 shows a canister 30 disposed on a rotating mechanism 32 on a moveable planar surface or shelf 40 according to a non-limiting embodiment. A plurality of ports 60 are disposed on an end cap 42 including an opposing end closure 61. Channel tubes 62 are inserted through corresponding ports 60. Said ports 60 and/or channel tubes 62 serve as passageways from the canister exterior to the interior volume of the canister. Although FIG. 7 shows ports 60 and channel tubes 62 disposed on the end cap 42 including an opposing end closure 61 which is fixed and not selectively removable from and attachable to the corresponding opposing end of the canister, in other non-limiting embodiments, one or more port(s) 60 and/or one or more channel tube(s) 62 are disposed on one or two end caps having one or more of the different types of the end cap configurations previously discussed. For a non-limiting example, one or more port(s) 60 and/or one or more channel tube(s) 62 are disposed on one or two end caps configured for selectively sealing and unsealing at least a portion of a corresponding end of the canister. The one or more ports and/or one or more channel tubes are configured for the selective passage of measurement instruments and/or supply and exit fluids respectively to and from an interior volume of the canister.

Figure 8A:
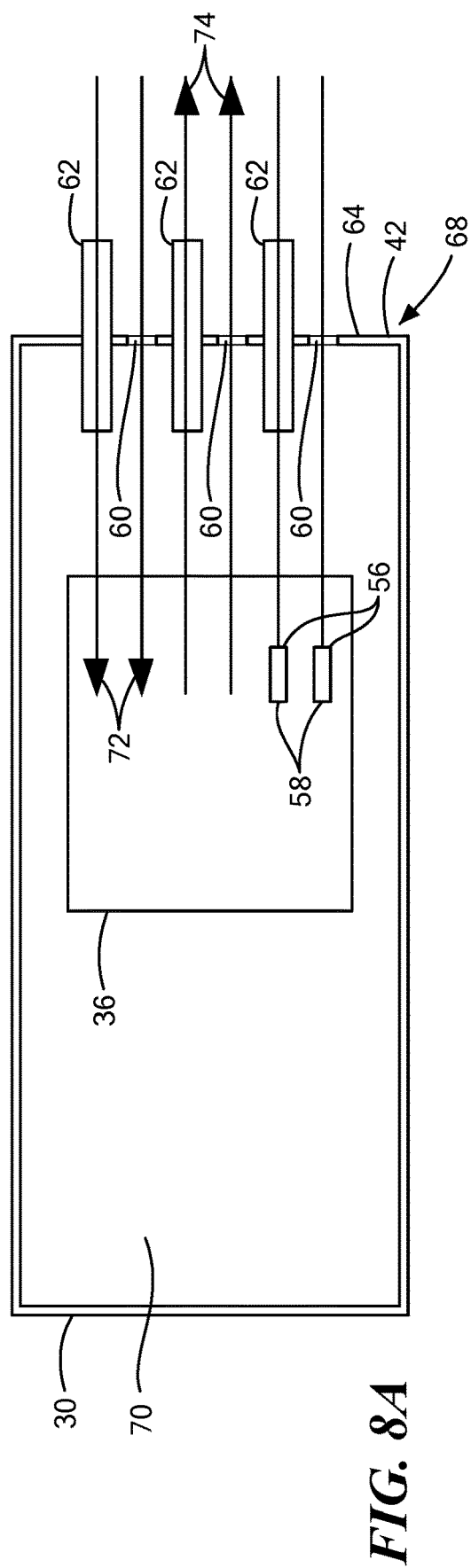
FIG. 8A shows a schematic of passage of measuring instruments and/or fluidic passage of supply and/or exit fluids respectively to or from an interior volume of a canister for containment of material for irradiation according to one non-limiting embodiment.

FIG. 8A shows a schematic of non-limiting embodiments wherein a product material for irradiation is contained within a canister. Port(s) 60 or channel tube(s) 62 are configured for selective passage of an instrument 56 and/or selective fluidic passage of a supply fluid 72 or exit fluid 74 respectively to and from an interior volume of the canister. The supply fluid 72 and the exit fluid 74 include respectively, for non-limiting examples, a supply gas and an exit gas. The ports 60 or the channel tubes 62 are disposed through a surface 64 or shell of the one or two canister end caps 42 thereby permitting selective passage of a first end 58 of an instrument 56 such as, for a non-limiting example, a probe, from the canister/drum exterior 68 to the interior volume 70 of the canister 30 or drum whereby the first end 58 of the instrument is proximate to the material 36 for irradiation. In other non-limiting embodiments, the one or more port(s) 60 or channel tube(s) 62 are disposed through an exterior surface 64 of one or more canister end cap(s) 42 to the interior volume 70 of the canister 30 and used for permitting or supplying a selected fluidic flow including a supply fluid 72 from the canister exterior 68 to the interior volume 70 of the canister 30 or drum. In still other non-limiting embodiments, the one or more port(s) 60 or channel tube(s) 62 are disposed through an exterior surface 64 or shell of the canister end cap 42 to the interior volume 70 of the canister for permitting a selected fluid fluidic flow including an exit fluid 74 from the interior volume 70 to the exterior 68 of the canister or drum for selective release or "burping" of exit fluid 74 or gases from the interior volume 70 of the canister 30 or drum.

Figure 8B:
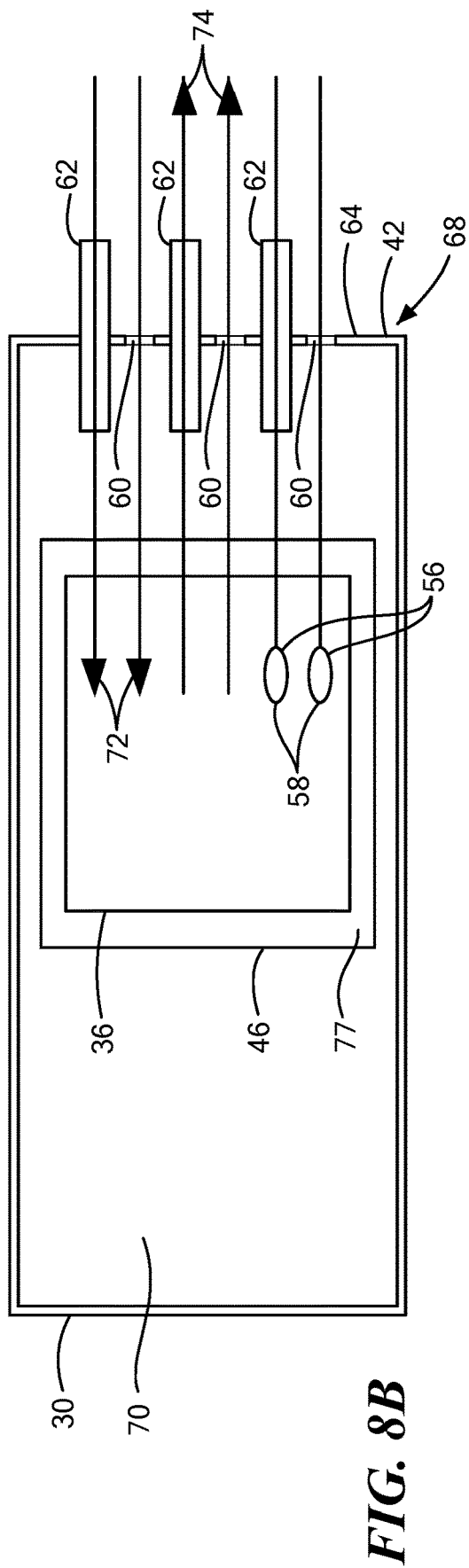
FIG. 8B shows a schematic of passage of measuring instruments and/or fluidic passage of supply and/or exit fluids respectively to or from an interior volume of a containment device for containment of material for irradiation disposed in a canister according to one non-limiting embodiment.

FIG. 8B shows a schematic of other non-limiting embodiments wherein a containment device containing product material for irradiation is contained within the canister. The one or more port(s) 60 or channel tube(s) 62 are disposed through an outer surface 64 of an end cap 42. A containment device 46 including a shell 76 is disposed in the interior volume 70 of the canister 30 or drum where the containment device 46 contains the product material 36 for irradiation. The ports and/or channel tubes are configured to permit selective passage of a first end of 58 of an instrument 56 from the canister exterior to the canister interior volume 70 surrounding the containment device 46. The ports and/or channel tubes are also configured to permit selective fluidic flow of a supply fluid 72 to and an exit fluid 74 from the interior canister volume 70 surrounding the containment device 46.

The schematic of FIG. 8B shows the supply fluid 72 selectively supplied to or the exit fluid 74 selectively withdrawn from the interior volume 77 of the containment device 46 surrounding the product material 36. The schematic of FIG. 8B additionally shows the selective passage of the first end 58 of instrument 56 into the interior volume 77 of the containment device 46 surrounding the product material 36.

FIG. 8B further shows the containment device being permeable to the supply or exit fluids. Thus, the supply fluid 72 is supplied to or the exit fluid 74 is withdrawn from the product material 36. FIG. 8B also further shows the containment device being permeable to the passage of the first end 58 of the instrument 56, wherein the first end 58 of instrument 56 is selectively passed into the product material 36.

Selective passage of the of the measurement instrument includes both insertion and withdrawal of the measurement instrument.

In other non-limiting embodiments, the containment device 46 and the one or more channel tubes 62 are configured to enable passage of a first end 63 of the one or more channel tube(s) 62 through the shell 76 of the containment device 46. Such channel tubes (62) thus enable selective passage of the first end 58 of the instrument 56 through the shell 76 of the containment device 46 to the interior volume 77 of the containment device 46 surrounding the product material 36 and optionally to the product material. Such channel tubes 62 also enable supply of a supply fluid 72 to and withdrawal of an exit fluid 74 from the interior volume 77 of the containment device 46 surrounding the product material 36 and the product material.

FIG. 8A and FIG. 8B show the port(s) and/or channel tube(s) disposed on an end cap of the canister, in alternative non-limiting embodiments, the port(s) and/or channel tube (s) are disposed on two end caps.

In other non-limiting embodiments, the ports 60 and/or the channel tubes 62 are used interchangeably for reversible insertion of instruments such as probes, and/or supplying or release of selected fluids such as gases. Each port and/or channel tube is configured having dimensions including an inside and an outside diameter and length selected for the preferred application or use including for example, supply of a supply fluid, withdrawal of an exit fluid, selective passage of a measuring instrument, and/or interchangeable use of the aforementioned.

In different non-limiting embodiments, each end cap of the canister, drum or other packaging is configured with one or more ports 60 and/or channel tubes 62, as discussed above. FIG. 7 shows an end cap including an opposing end closure canister end closure 61 with a series of ports 60 disposed at various selected radii 74 relative to the rotating canister's isocenter 54. In alternative non-limiting embodiments, one or more channel tubes 62 are inserted into said ports and thus disposed at selected radii 74. In preferable embodiments, the one or more port(s) 60 and/or the one or more channel tubes 62 are disposed on the end cap 42. Each port 60 or channel tube 62 can be used for the insertion of a first end 58 of an instrument 56 such as, for a non-limiting example, a dosimeter, as shown in the non-limiting example of FIG. 6 thus enabling measurements at selected radii 74 relative to the canister isocenter 54. The non-limiting example of a typical radiation dosimeter probe shown in FIG. 6 includes ink markings along the probe which designate the depth of probe insertion into the canister. The one or more ports 60 and/or channel tubes 62 can be disposed at various selected locations on the endcap. For a non-limiting example, the one or more ports 60 or channel tubes 62 can be disposed at the isocenter 54 of the end cap or along the distal edge 76 of the end cap and/or at other various locations on the end cap or opposing end closure. The instruments inserted via the ports 60 and/or channel tubes 62 can be used to measure the conditions at various positions in the interior of the canister, drum, or other packaging. For non-limiting examples, a dosimeter can be used to measure and record radiation the dose being delivered to the irradiated material, and a temperature or humidity probe respectively material temperature or moisture. The ports 60 and/or channel tubes 62 can be open or can be selectively and thus reversibly sealable. The same or different one or more ports 60 and/or channel tubes 62 can be used to vent or circulate gases respectively from or to the canister 30, drum or other packaging before, during, and/or after the irradiation process.

Each of the one or more canisters or drums is placed on a corresponding rotating mechanism or stage 32, as shown in for a non-limiting example FIG. 2. The rolling or rotating mechanism or stage rotates or rolls the respective canister 30 or drum about the container's own central horizontal or longitudinal axis 34 as shown in FIG. 2. The product material 36 contained within the canister or drum is thus passed through the irradiation volume 38 such as an X-ray beam as shown in FIG. 4. The rotating mechanism 32, rotation or auto roll feature facilitates and/or increases dose uniformity throughout the volume of the irradiated product material 36. This rotating mechanism 32, rotation or auto roll feature which gently rotates the canister 30 or drum through irradiation such as an X-ray treatment process enables increased dose uniformity and decontamination of the irradiated product material 36 while simultaneously preserving the integrity of the look, smell and feel of the irradiated product material 36 including, for non-limiting examples, flowers.

Figure 9C:
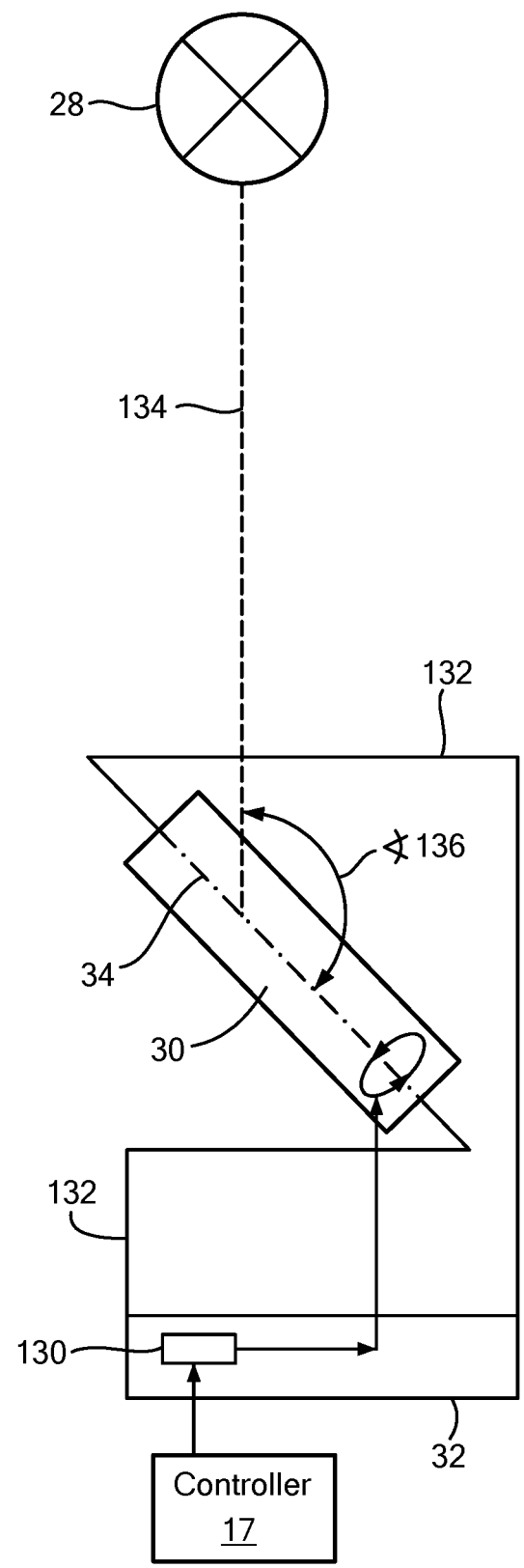
FIG. 9C shows a schematic of a rotating mechanism which incorporates a rotating mechanism control technology according to one non-limiting embodiment.

In non-limiting embodiments of the invention, the rotating or rolling mechanism or stage 32 incorporates a rotating mechanism control technology 130, as shown in the schematics of the non-limiting embodiments of FIGS. 9A, 9B and 9C. The rotating mechanism control technology 130 is configured for selectively modulating or adjusting the operating parameters of the rotating mechanism 32. The controller 17 is integrated and communicates with and controls the rotating mechanism control technology 130.

Rotating mechanism operating parameters which can be selectively adjusted, controlled, and optimized include for a non-limiting example the rotation speed. Rotation speed is adjusted for achieving a uniform or more uniform distribution of radiation dose throughout the product material including for non-limiting examples dense and/or packed ground product material.

Rotating mechanism operating parameters which can be selectively adjusted, controlled, and optimized also include the canister orientation with respect to a select radiation beam. FIGS. 9A, 9B and 9C show the rotating mechanism control technology 130 is integrated with a canister orientation mechanism 132 which is configured for selectively setting and/or varying or tilting an orientation of the canister with respect to a select radiation beam 134. In one non-limiting example, the rotating mechanism control technology 130 is used to control the canister orientation mechanism 132 to dispose selectively the canister 32 in a "rolling position" wherein the longitudinal axis 34 of the canister is disposed substantially orthogonal relative to a select radiation beam 134 of radiation source 28, as shown in the schematic of FIG. 9A. In a second non-limiting example, the rotating mechanism control technology 130 is used to control the canister orientation mechanism 132 to dispose selectively the canister 30 in a "spinning position" wherein the longitudinal axis 34 of the canister 30 is disposed substantially in parallel with the select radiation beam 134, as shown in the schematic of FIG. 9B. In a third non-limiting example, the rotating mechanism control technology 130 is used to control the canister orientation mechanism 132 to dispose selectively the canister 30 wherein the longitudinal axis of the canister is disposed substantially at an angle as shown by angle 136 in the schematic of FIG. 9C. The angle 136 fails which falls within a range of 0 to 180 degrees relative to the select radiation beam 134. The select setting and/or variation of the canister orientations relative to the radiation source can be used to optimize the radiation of the product material or sample contained within the canister. For a non-limiting example, the selective setting and/or variation of the canister orientation relative to a select radiation beam can be used to compensate for variations in the radiation beam including the anode heel effect. The controller 17 is integrated with and controls that the rotating mechanism control technology 130 which in turn controls the rotation speed and the canister orientation via the canister orientation mechanism 132.

In non-limiting embodiments of the invention, the rotating mechanism control technology is integrated with a control technology including for non-limiting examples, imaging control technology, optical control technology, electromagnetic control technology for closed-loop control, and/or electromagnetic control technology for semi-closed loop control and/or a combination or two or more of the previously mentioned control technologies. Imaging control technology includes for a non-limiting example, a camera taking a picture or sequence of pictures of the canister or drum during rotation and integrating this information with the rotating mechanism control technology. Alternatively or in addition, imaging control technology includes radiation detection discussed further below. Optical control technologies include, for a non-limiting example, LED type sensors integrated with the control technology. Other motion control technologies known to those of ordinary skill in the art can also be used with the invention. The modulation, adjustment and/or selective control of the rotation speed and motion of the rolling or rotation motion and orientation of the canister can be continuous or non-continuous.

Figure 9D:
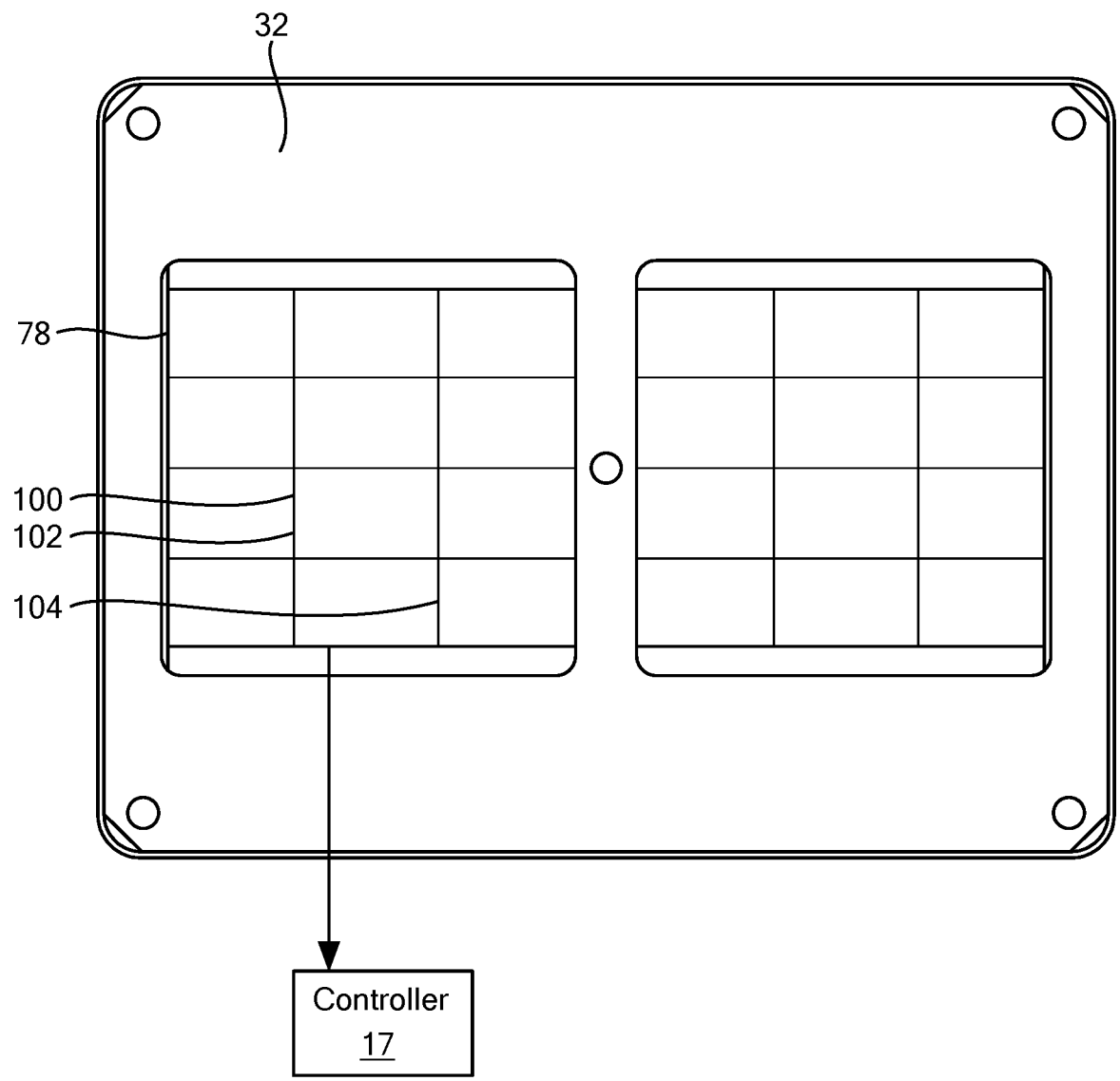
FIG. 9D shows a bottom view of a rotating mechanism having two clearance portions configured for disposition of one or more types of control technologies according to one non-limiting embodiment of the invention.

In a non-limiting embodiment, the rolling or rotating mechanism or stage is configured having a one or more clearance portions 78, as shown in FIG. 9D. The clearance portions are configured for disposition of one or more types of control technologies 100. In a non-limiting embodiment, the clearance portions 78 are configured for disposition of one or more imaging control technologies 102 including one or more radiation detectors 104. The radiation detectors are configured for detecting radiation passing through the product material or sample contained within the canister and creating one or images during canister rotation and/or imaging the irradiation volume 38 shown for example in FIG. 4. For purposes of the application, the phrase "imaging the irradiation volume" refers to the obtaining of information about properties of the product material or sample within the irradiation volume 38. For example, the control technology including an imaging control technology 102 including one or more radiation detectors 104 can be configured to determine properties including density and/or distribution of the irradiated material based on the detection of radiation passing through the irradiated product material during the rotation of the canister about its axis. X-rays travel in straight lines, emerging as a beam from the radiation source. X-rays will either travel through materials with a varying degree of attenuation (e.g., non-metal materials) or will be scattered or absorbed by certain materials, such as metal. The amount of radiation that is received at a detector is indicative of the properties of the same such as for example material type and/or density. The radiation source is typically operated at a relatively lower power level for imaging purposes. The radiation levels used for imaging are typically significantly lower that the radiation levels used for irradiation. Imaging data can be repeatedly or continuously acquired.

FIG. 9D shows a bottom view of a canister rotating stage or roll mechanism 32 having clearance portion 78 including two cut-out "windows" to allow for the placement of control technology 100. The control technology 100 includes an imaging control technology 102 including a radiation detector 104 such as an X-ray detector positioned within each clearance portion 78 according to a non-limiting embodiment. In other non-limiting embodiments, the rotating mechanism include one or more than two cut out windows according to the needs of the application.

The controller 17 is configured to integrate information from received from the control technology 100 including for a non-limiting example, imaging control technology 102 including radiation detectors 104. Based on one or more projection images developed from the detection of radiation passing through the irradiated material, the controller calculates information regarding the properties of the irradiated product material such as for non-limiting examples material density and/or distribution, and integrates such information to adjust or modify and/or optimize the selected irradiation data plan for the radiation source, the positioning of the product material within the canister via the securing and/or dimensional depth components, and/or the operating parameters for the rotating mechanism and the programmable shelf discussed further below.

In non-limiting embodiments, the radiation detector 104 includes a plurality of detectors which are capable of detecting radiation such as X-ray or other radiation. The control technology 100 including for a non-limiting example the imaging control technology 102 including radiation detector 104 extends over substantially all or only part of the clearance portion 78. The radiation detector 104 includes one, a plurality and/or a grid of detector elements or devices which provide pixels of an image according to a non-limiting embodiment. The output of the radiation detector 104 is connected to readout circuitry.

The controller 17 controls operation of the control technology 100 as shown in FIG. 9D and the radiation source 28 as shown in FIG. 4. The control of the radiation source includes control over switching the radiation source 28 on and off and control of the irradiation data plan. The irradiation data plan includes one or more of the following operating parameters:

- a total radiation dose (gray or Gy corresponding to the absorption of one joule of radiation energy per kilogram of matter);
- a rate of radiation delivery (rem (roentgen equivalent man) or millirem ($1/1000^{th}$ of a rem) per unit time typically measured in minutes or hours) including whether said rate of radiation delivery is fixed, or varying over a total duration of the irradiation cycle;
- a total duration of the irradiation (typically measured in minutes or hours);
- a radiation output by an activated radiation source including whether said output is fixed, or varying over a total duration of the irradiation cycle, where radiation output is determined by (i) tube current to control energy per photon and (ii) tube voltage V2 to control energy per photon;
- a beam angle of the activated radiation including whether said beam angle is fixed or varying over a total duration of irradiation cycle. The beam angle is controlled by a collimator.

The controller 17 is positioned in the same cabinet 12 or separately from the cabinet 12 as shown in FIG. 1.

In a non-limiting embodiment, the controller 17 includes software and a processing apparatus configured to provide an irradiation data plan based on information about the material for irradiation and regulatory standards for a particular jurisdiction. Relevant information about the pre-irradiated product material or sample includes one or more of the following data:

material type including for non-limiting examples identification solid or liquid material, and/or plant or non-plant-based material;
material consistency including for non-limiting examples identification of whether the material includes loose or tightly packed material on a scale of 1-10 where 1 is loose material and 10 is tightly packed material, and/or flower, bud or powder material;
material weight;
material volume;
material density; and/or
microbial contamination data by weight or volume.

Figure 10:
FIG. 10 shows a non-limiting example of laboratory report including information about a product material including a machine-readable information QR code.

In different non-limiting embodiments, the information about the material for irradiation is acquired by the irradiation system using one or more of the following methods. Data including information about the material and/or a particular batch of material is input by the system operator based on the system operator's direct observation (e.g., material type or consistency), based on the system operator's measurements (e.g., weighing the material for irradiation using an external scale or other weighing mechanism, or a scale or other weighing mechanism which is incorporated into the irradiation system, as further described below), or based upon a description or report describing the material provided by, for non-limiting examples, the provider of the material for irradiation and/or the canister or containment device fabricator, and/or a laboratory which has tested, analyzed and/or otherwise evaluated the material for irradiation. The irradiation system operator inputs the data including information about the material into the software and processing apparatus of the irradiation system via the user interface or the data input is received by the system from another apparatus or system component. In non-limiting examples, a laboratory or other report describing the material, and/or the canister and/or a containment device containing the material for irradiation, includes a bar code, a QR code or other type of machine-readable information code associated with material for irradiation and/or a particular batch of the material. FIG. 10 includes a non-limiting example of laboratory report including information about a product material for irradiation including a machine-readable QR information code. Upon scanning of the report and/or the machine-readable information code, information about the material for irradiation and/or batch of material is acquired by the software and processing apparatus of the irradiation system. The irradiation system is configured with a scanning mechanism such as a scanning wand or scanning window disposed on an exterior or in an interior of the cabinet which the system operator uses for the scanning the report and/or code. Alternatively, when the canister is inserted into an interior of the cabinet and/or chamber, the interior of the cabinet and/or chamber is configured with an interior scanning mechanism which scans a machine-readable information code disposed on for a non-limiting example an exterior surface of the canister, and the software and processing apparatus of the irradiation system acquires information about the material. In another non-limiting embodiment, at least one of the rotating mechanism, the programmable shelf which is described further below or other system component is configured to include a weighing mechanism. When the canister is disposed on the respective rotating mechanism, programmable shelf, or other component, the software and processing apparatus of the irradiation system provides a digital output of the weight which the system operator inputs into the software and processing apparatus of the irradiation system. In a non-limiting embodiment, the weighing mechanism is integrated with the software and processing apparatus. The software and processing apparatus acquires the weight of the canister or canister enclosing a containment device containing the material from the integrated weighing mechanism and calculates the weight of the material.

Material type and/or consistency. Data including information about the material type and/or consistency is based on direct observation by the system operator or based upon a description or report describing the material provided by for non-limiting examples the provider of the product material and/or a laboratory which has tested, analyzed and/or otherwise evaluated the material. Data regarding material type and/or consistency is input by the operator via the user interface and/or is obtained through scanning the report about the material or particular batch of material and/or is obtained through a machine-readable information code included in the report or disposed on a canister or containment device containing the material for irradiation as described above.

Material weight: A first weight for the empty canister or empty canister and empty containment device and a second weight for the canister or canister and containment device containing the material or sample for irradiation are obtained. The weights are obtained through the use of an external scale or via a weighing mechanism incorporated into for non-limiting examples the rotating mechanism, the programmable shelf, or other component of the irradiation system. The external scale and/or incorporated weighing mechanism is integrated with the system software and processing apparatus such that the irradiation system directly acquires the weight information from the external scale or incorporated weighing mechanism. Alternatively, the external scale and/or weighing mechanism include a digital or other readout from which the system operator can record and/or input said data into the system via the user interface. Alternatively, corresponding pre-recorded first and/or second weights are obtained through scanning a report about the material or particular batch of material and/or machine-readable information code included in the report or disposed on an exterior of a canister or containment device containing the material for irradiation as described above. The weight of the product material or sample for irradiation is calculated by subtracting the weight of the empty canister or empty canister and empty containment device from the weight of the corresponding canister or canister and containment device containing the product material or sample. The calculation is conducted by the software and processing apparatus of the system. Alternatively, the irradiation system operator performs the weight calculation and directly inputs the data including the weight of the product material or sample for irradiation via the user interface.

Material volume: The irradiation system operator determines the volume of the canister or containment device for the product material or sample for irradiation and inputs said volume data into the irradiation system software via the user interface. For a non-limiting example, if product material is contained within a 10-gallon canister or drum, the operator inputs the volume data as 10 gallons into the irradiation system software via the user interface. Alternatively, the material volume is obtained through scanning a report about the material or particular batch of material and/or machine-readable information code included in the report or disposed on an exterior of the canister or the containment device containing the material for irradiation as described above.

Material density: The software and processing apparatus of the irradiation system software calculates a pre-irradiation overall density of the product material or sample by dividing the weight by volume data.

Microbial contamination data by weight or volume: Microbial contamination data by weight and/or volume includes one or more of the following data for a particular sample or batch or product material:

total aerobic count including *Aspergillus* unspecified, bile-tolerant gram-negative, *Staphylococcus aureus*, total yeast and mold, *E. coli*, total Enterobacteriaceae, *Pseudomonas aeruginosa, Salmonella* spp., Shiga toxin-producing *E. coli* (STEC), total Coliform, *L. monocytogenes;*
    total aerobic microbial count;
    total yeast count;
    total mold count;
    coliform;
    bile-tolerant gram-negative bacteria;
    *Aspergillus flavus;*
    *Aspergillus fumigatus;*
    *Aspergillus niger;*
    *Aspergillus terreus;*
    *Salmonella;*
    Shiga toxin-producing *E. coli* (STEC);
    *Candida Albicans;*
    Total plate count for aerobic bacteria An assay is conducted on the product material or sample to determine one or more of the above microbial contamination data for a product material or sample for irradiation. The irradiation system operator then inputs the one or more microbial contamination data for the particular product material or sample into the irradiation system software via the user interface. Alternatively, information about the product material or sample including microbial contamination data by weight or volume is obtained through scanning a report about the material or particular batch of material and/or machine-readable information code included in the report or disposed on a canister or containment device containing the material for irradiation as described above.

Target Microbial Contamination Regulatory Standards for the Target Jurisdiction

The irradiation system operator then selects and/or enters the target jurisdiction such as a state, county, district, or city, as necessary, where distribution of the product material or sample is targeted, intended or anticipated. The irradiation system software accesses and/or acquires the target microbial contamination regulatory standards for the target jurisdiction. The target microbial contamination regulatory standards are pre-entered into the irradiation system software and updated periodically as necessary by, for non-limiting examples, the irradiation system operator or administrator. Alternatively, the irradiation system software is designed to access and/or acquire electronically the applicable microbial contamination regulatory standards from, for a non-limiting example, the target jurisdiction's regulatory agency's website. In another non-limiting example, the irradiation system operator directly inputs data including the relevant particular target microbial contamination regulatory standards into the irradiation software via the user interface at the time of processing the product material or sample.

Based on a comparison of the information about the pre-irradiated product material or sample inputted into the irradiation system software and the target microbial contamination regulatory standards, the irradiation system software determines an irradiation data plan for the particular product material or sample for irradiation. In a non-limiting embodiment, the irradiation system software includes one or more options for optimizing the irradiation plan according to one or more optimizing requirements selected by the irradiation system operator. The optimizing options include for non-limiting examples, a minimum total radiation dose or the least amount of radiation required, a minimum total irradiation duration or the least amount of irradiation time required, and/or a combination of the aforementioned optimizing options. For a non-limiting example, responsive to a prompt initiated by the irradiation system software, the irradiation system operator selects an optimizing option including minimum total radiation duration. The irradiation system software then determines the optimum irradiation data plan including the necessary irradiation parameters for achieving the targeted microbial contamination regulatory standards for the irradiated product material or sample in the minimum total irradiation duration.

The one or more rotating mechanism(s) 32 are disposed on one or more shelves 40 preferably including planar surfaces, as shown in FIG. 7. In a preferred embodiment, the shelf 40 includes control technology and is programmable for selective positioning through selective control of the operating parameters for the shelf. The programming of the control technology is integrated with and controlled by the controller 17. Each shelf can be controllably positioned at a selected height to achieve a selected distance from and/or at a selected orientation or tilt relative to the irradiation or ionizing radiation source to optimize irradiation of the material. The selective positioning of the programmable shelf accommodates different batch volumes and multiple canister and containment device sizes. The irradiation system 10 includes a motor (not shown) to drive the movement of the shelf 40.

Figure 11A:
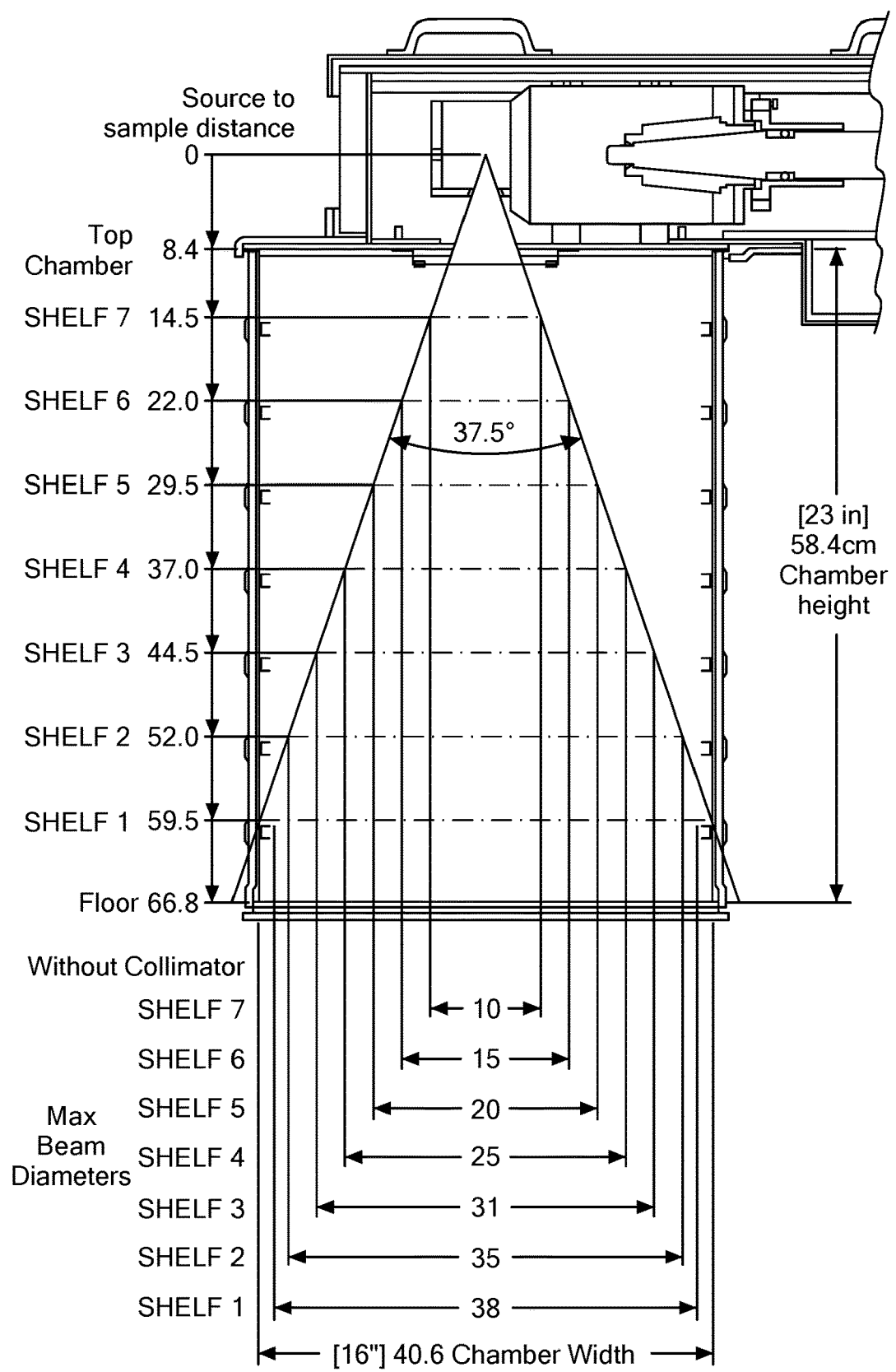
FIG. 11A shows shelf positions and beam coverage for the irradiation system according to non-limiting embodiments.

FIG. 11A shows the shelf positions and beam coverage for a non-limiting embodiment of the programmable moveable shelf for the irradiation system of the invention. The angle of the irradiation beam is 37. 5°. The height and width of the chamber are respectively 58.4 cm. and 40.6 cm.

| Shelf | Distance from radiation Source to Sample (cm.) | Max Beam Diameter without collimator (cm.) | Max Square Size with collimator (cm.) | Max Rectangle Size with collimator (cm.) |
|---|---|---|---|---|
| Chamber Top | 8.4 | | | |
| 7 | 14.5 | 10 | 10.5 × 10.5 | |
| 6 | 22.0 | 15 | 14.0 × 14.0 | 13.0 × 7.5 |
| 5 | 29.5 | 20 | 18.0 × 18.0 | 17.0 × 10.0 |
| 4 | 37.0 | 25 | 21.5 × 21.5 | 21.0 × 12.5 |
| 3 | 44.5 | 31 | 25.5 × 25.5 | 26.0 × 15.5 |
| 2 | 52.0 | 35 | 27.0 × 27.0 | 30.0 × 18.0 |
| 1 | 59.5 | 38 | | 34.0 × 17.0 |
| Floor | 66.8 | 40.6 | | |

Figure 11B:
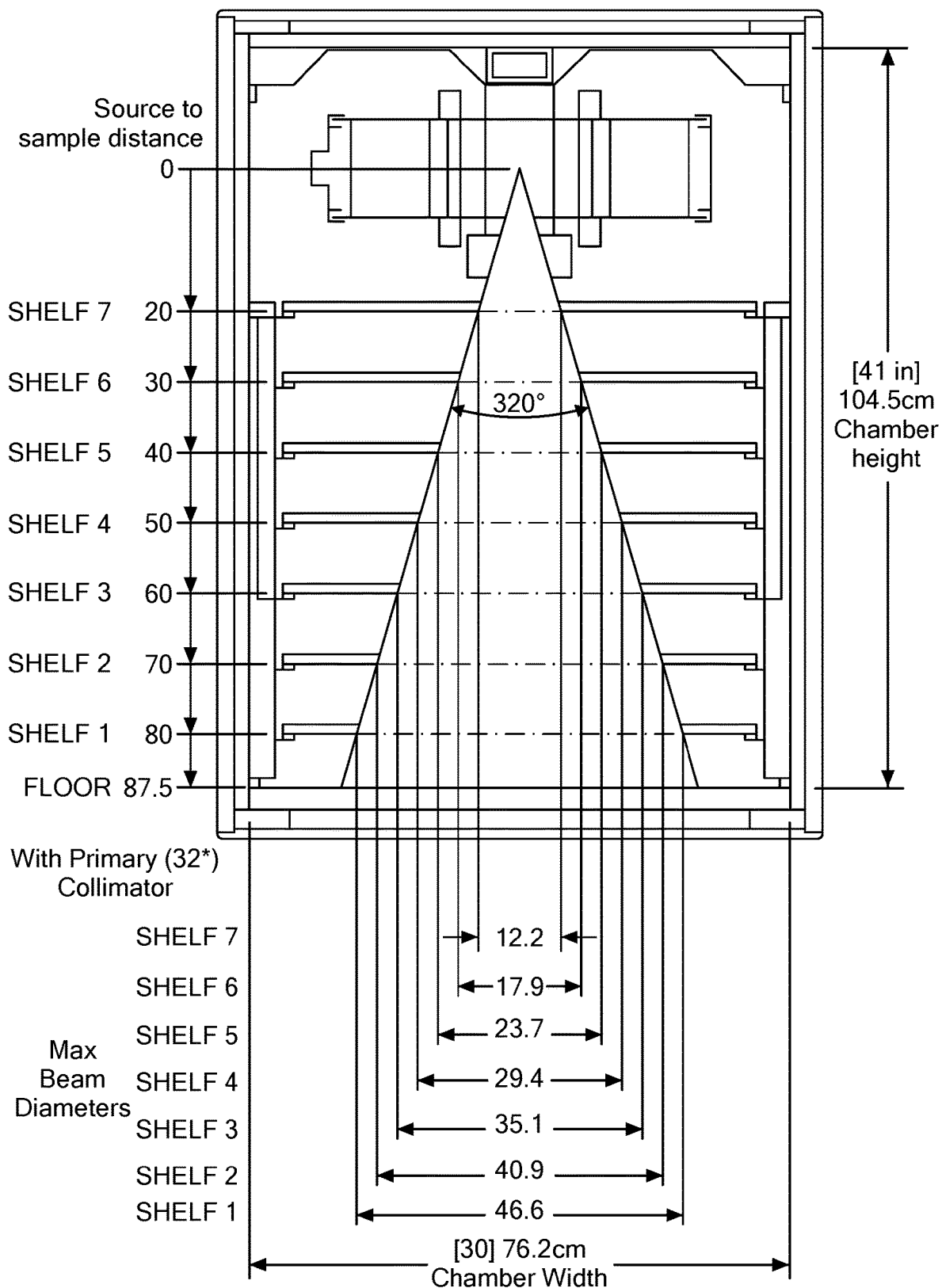
FIG. 11B shows shelf positions and beam coverage for the irradiation system according to non-limiting embodiments.

FIG. 11B shows the shelf positions and beam coverage for another non-limiting embodiment of the programmable moveable shelf for the irradiation system of the invention. The angle of the irradiation beam is 32. 0°. The height and width of the chamber are respectively 104.5 cm. and 76.2 cm.

| Shelf | Distance from radiation Source to Sample (cm.) | Maximum Beam diameter with 32° collimator (cm.) |
| --- | --- | --- |
| 7 | 20 | 12.2 |
| 6 | 30 | 17.9 |
| 5 | 40 | 23.7 |
| 4 | 50 | 29.4 |
| 3 | 60 | 35.1 |
| 2 | 70 | 40.9 |
| 1 | 80 | 46.6 |
| Floor | 87.5 | |

Thus, the irradiation system includes multiple opportunities, alternatives and/or possibilities for setting and/or adjusting irradiation treatment according to particular materials or batches of material for irradiation and modifying and/or fine tuning said irradiation according to the regulatory standards of a target jurisdiction. The system further provides options for optimizing said irradiation in view of for non-limiting examples minimum radiation dose or minimum irradiation duration. The combination of multiple opportunities for adjustment, fine-tuning and optimization enable the processing of high volumes of material including varied batches of material having differing product characteristics and/or regulatory requirements in the most efficient manner possible.

Figure 12:
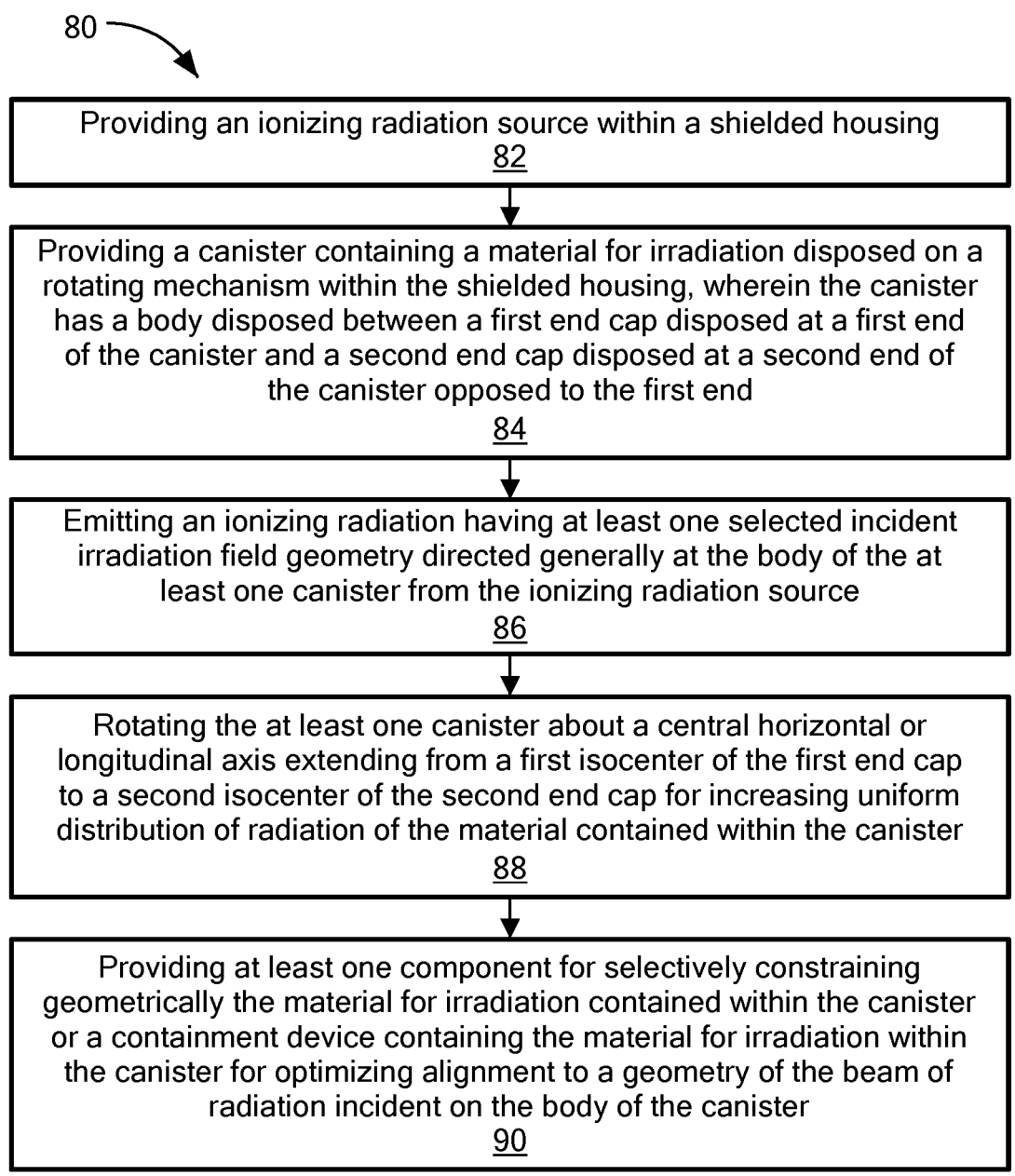
FIG. 12 shows a schematic corresponding to a method of operating the irradiation system according to one non-limiting embodiment.

In another aspect, the invention provides a method of irradiation of a material, as shown in the non-limiting embodiment shown in FIG. 12. The method 80 includes providing an ionizing radiation source within a shielded housing as shown in step 82. The method also includes providing at least one canister containing a material for irradiation disposed on a rotating mechanism within the shielded housing, as shown in step 84. The provided canister has a body disposed between a first end cap disposed at a first end of the canister and a second end cap disposed at a second end of the canister opposed to the first end. The method includes emitting an ionizing radiation having at least one selected incident irradiation field geometry directed generally at the body of the at least one canister from the ionizing radiation source, as shown in step 86. The method further includes rotating the at least one canister about a central horizontal or longitudinal axis extending from a first isocenter of the first end cap to a second isocenter of the second end cap for increasing uniform distribution of radiation of the material contained within the canister, as shown in step 88.

In a non-limiting embodiment, the method includes providing at least one component for selectively constraining geometrically the material for irradiation contained within the canister or a containment device containing the material for irradiation within the canister for optimizing alignment to a geometry of the beam of radiation incident on the body of the canister, as shown in step 90. In non-limiting embodiments, the at least one component is selected from the group consisting of a securing component and a dimensional depth component; is disposed on at least one of the first end cap and the second end cap; and/or is selectively flexibly expandable and contractable. In a preferred embodiment, at least a portion of at least one of the first end cap and the second end cap is configured for selectively sealing and unsealing at least a portion of a corresponding opposing end of the canister. an interior volume of the canister.

Figure 13:
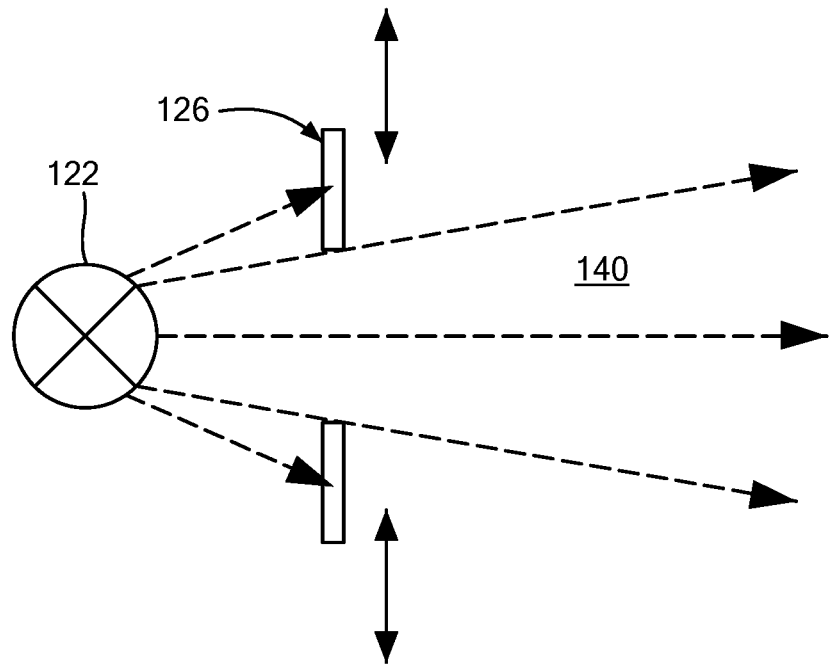
FIG. 13 shows a radiation source and a beam controlling device or collimator according to one non-limiting embodiment.

FIG. 13 shows a radiation source 122 corresponding to the radiation source shown by element 28 in inter alia FIG. 4 and a beam controlling device or collimator 126 according to a non-limiting embodiment of the invention. The beam controlling device 126 can be controlled to vary a size of an opening or aperture. This controls shape and/or width of a beam of radiation emitted by the radiation source 122 towards the irradiation volume 140 corresponding to the irradiation volume shown by element 38 in inter alia FIG. 4. A beam controlling device 126 can be provided for the radiation source 122. It is to be understood that the ability to acquire images of a sample enables information regarding a variation in density of a sample within the sample to be obtained. It also provides information regarding volumetric and spatial distribution of the sample to be determined. The relative location of the product material or sample packaging including the canister and optional containment device can also be determined. This increased understanding of density with volumetric and spatial distribution information made available by embodiments of the present invention can be advantageous for certain applications.

Firstly, X-ray radiation having an energy below around 300 kV has been shown to be more effective in microbial remediation than higher energy sources (such as gamma radiation and high energy X-ray radiation). However, at these lower energies, the X-ray absorption and scatter by samples is much greater and therefore the radiation does not penetrate through as much of the sample in as uniform a way as with high energy gamma and X-ray sources.

The increased absorption and scatter of these lower energy X-rays will cause the dose delivered to the samples and sample packaging at different densities, volumes and spatial distributions to vary much more significantly than higher energy gamma and X-ray sources. Care in planning the dose delivery to the sample is therefore much more important and the described imaging steps can enable a plan for uniform low energy X-ray dose delivery to all parts of the sample to be created relatively quickly.

Secondly, the imaging step allows optimization of power (energy saving) and throughput by ensuring that the required dose is reached for all parts of the sample with limited amounts of the sample receiving more dose than is required. This is also be described as an improved Dose Uniformity Ratio.

Thirdly, many types of produce such as meats, fruits. spices and vegetative crops such as cannabis can have multiple types of packaging material surrounding the sample to be irradiated and these packaging changes must be considered when determining dose levels to be applied to the samples. Thus, the amount of absorption of X-ray radiation by the packaging is taken into account in some non-limiting embodiments, and the dose of X-ray radiation to which the item (sample and packaging) is subject is adjusted accordingly in order to ensure that the required dose to the sample, within the packaging, is achieved. The amount of absorption of X-ray radiation by a canister or an optional containment device contained with the canister associated with the irradiation system 10 can be taken into account in some non-limiting embodiments, and the dose of X-ray radiation to which the canister, optional containment device and product material or sample is subject can be adjusted accordingly in order to ensure that the required dose to the product material or sample within the canister and within the optional containment device is achieved.

Fourthly, X-ray irradiation of the samples in the desired end product packaging has the advantage that downstream handling of the samples is made easier since a reduction in the risk of recontamination of the sample during downstream handling may be achieved.

Fifthly, customers looking to use X-ray irradiation systems and devices according to embodiments of the present invention for sterilization may wish to irradiate samples that vary greatly in density, as well as in volume and spatial distribution of the sample in the irradiation field, but which also vary greatly in the density and spatial distribution of the different packaging types that they use with samples. The determination of the dose based on imaging taken as the canister rotates about an axis allows the user to compensate for both variations in sample density and spatial distribution as well as the nature of the sample packaging such as packaging material composition and thickness. The user may therefore use the system to irradiate a range of different sample types and different sample packaging materials whilst still providing the desired dose to substantially the entire sample based on the analysis of the imaging results.

It is to be understood that the irradiation and the imaging can be performed using the same radiation source allowing for a more simple and lower cost irradiation system and leading to improved workflow and throughput.

It is to be understood that packaging of the sample may create areas of higher density and lower density of materials surrounding the product material or samples for irradiation, and these areas can be detected by X-ray imaging. For example, a sample may be packaged in multiple sealed containment devices that are held within a canister side by side or stacked on top of each other or both. An irradiation system can also hold multiple canisters on the same shelf or on multiple shelves. The beam that is used to irradiate the sample will encounter different densities of materials in the packaging and in the samples contained in the packaging based on the density and number of canisters and optional containment devices that the beam projected from the radiation source encounters as it passes through the one or more canisters. Each beam will also encounter different densities of materials due to the different packaging materials used in each canister and optional containment device. For example, plastics or metal covers disposed on the top and/or ends of the canisters or optional containment devices have different densities as compared to materials such as plastic, glass, cardboard and/or other materials used in other parts of the canister or optional containment devices.

The systems, devices and methods according to embodiments of the invention are configured to enable a determination of a required amount of irradiation to which the irradiation volume is to be subject in order to deliver the required dose of radiation to the sample(s). In some non-limiting embodiments, the systems and/or devices according to embodiments of the invention are configured to enable a determination of the amount of radiation to which the irradiation volume is to be subject as the sample is rotated in the irradiation volume 38 in order to deliver the required dose to different regions of the sample. The system according to embodiments of the invention is equipped with the control technology integrated with the controller for controlling the X-ray radiation sources to deliver the required dose to the different regions of the sample. For example, a denser region of the sample may receive more radiation. In some non-limiting embodiments, regions of a sample with a higher moisture content may receive a higher dose than regions with a lower moisture content in order to compensate for absorption of radiation by the moisture. Similarly, where radiation is directed to pass through one or more canisters and optionally one or more containment devices and/or one or more shelves or other structural elements within the irradiation volume, the systems, devices and methods according to embodiments of the invention can take such items into account in determining the required amount of radiation to be delivered by a given radiation source at a given moment in time as the canister is rotated about an axis. In some non-limiting embodiments the sample is moved intermittently or at a speed that varies as a function of time in order to ensure that the required dose is delivered.

In addition, it is expected that in some cases a user may wish to irradiate the sample inside the final packaging in a sealed state so the sample inside the container, after the irradiation process is completed, can be considered fully decontaminated within the final packaging and no further manipulation of the sample and potential re-contamination can occur prior to the sample being delivered or purchased by the consumer.

In some non-limiting embodiments, in addition to or in lieu of determining an amount of X-ray radiation to which an irradiation volume is to be exposed, compensating for X-ray absorption due to packaging such as canisters or containment devices, or other elements of the system or devices such as the rotating mechanisms or shelves, based on acquired image data, the system or device can determine the amount of radiation to be applied to the irradiation volume at least in part based on data input by a user. For example, the user can input data such as data indicative of the type of packaging material (e.g. indicative of material and thickness) of the canisters or optional containment devices and/or the type, number, and positioning of canisters, optional containment devices, and other elements (e.g., the rotating mechanisms and shelves) disposed in the irradiation volume. The system and devices according to embodiments of the invention can be configured to apply a correction to the amount of X-ray radiation applied to the irradiation volume based at least in part on the data input by the user and stored data, such as data indicative of the amount of radiation absorbed by a given type of canister and/or optional containment device and/or other elements (e.g., the rotating mechanisms and shelves) disposed in the irradiation volume. Thus, the systems and devices compensate for an amount of radiation applied to the irradiation volume that would not irradiate the sample due to absorption or scattering by the containers, optional containment devices, and other elements disposed in the irradiation volume by increasing the amount of radiation applied in a corresponding manner.

Figure 14:
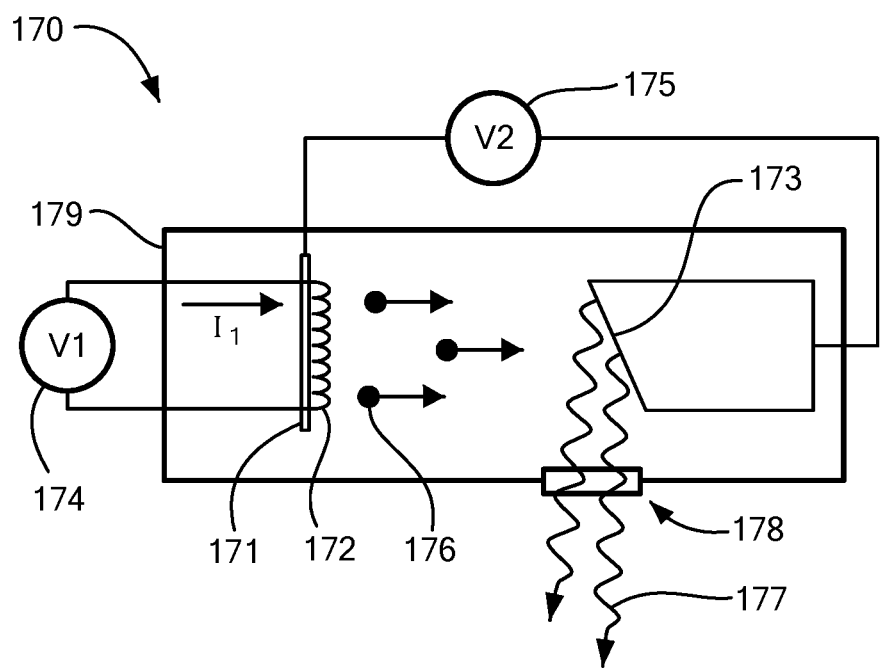
FIG. 14 shows an example of a radiation source including a reflection type X-ray tube which can be used to provide a beam of radiation through a side window according to a non-limiting embodiment.
Figure 15:
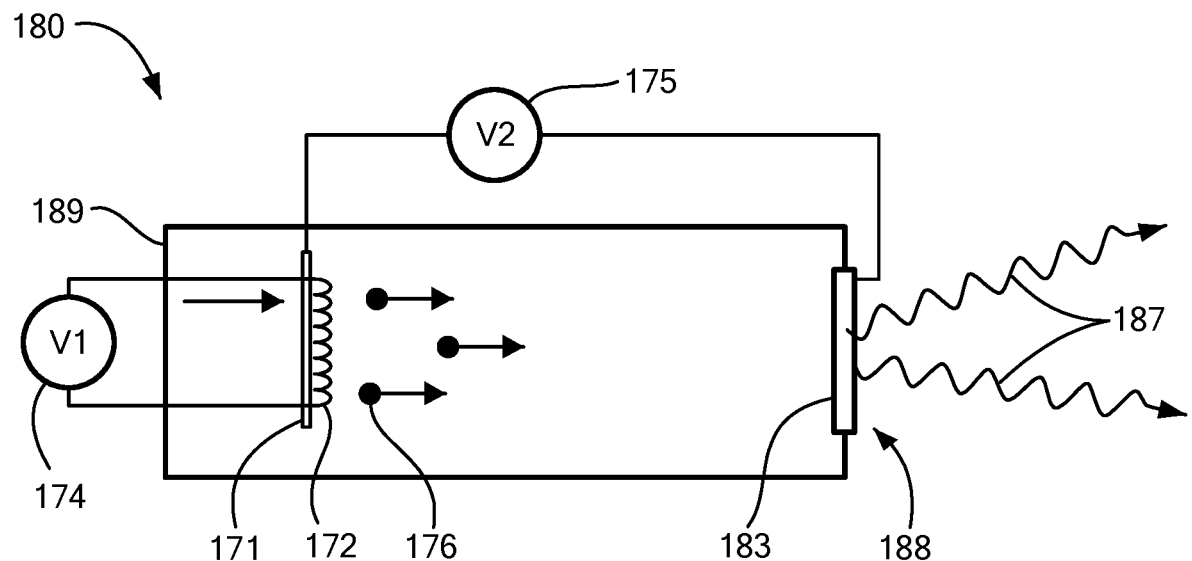
FIG. 15 shows an example of a radiation source including a transmission type X-ray tube which can be used to provide a beam of radiation according to one non-limiting embodiment.

FIGS. 14 and 15 show examples of two types of X-ray tube 170, 180 which can be used to provide a beam of radiation in non-limiting embodiments of the invention. FIG. 14 shows an example x-ray tube 170 which emits X-rays 177 through a side window 178 forming abeam of radiation. This type of x-ray tube 170 is called a Coolidge type x-ray tube or a reflection type x-ray tube. The x-ray tube 170 has a cathode 171, a filament 172 and an anode 173. A power supply 174 is connected to the filament 172. The filament 172 is typically made of metal with a high melting point. The power supply 174 is configured to supply a voltage V1 across the filament 172. An electrical current 11 flows through the filament 172. This is called the tube current. The current flow heats the filament and causes the filament to emit electrons 176 by thermionic emission. A power supply 175 is connected to the cathode 171 and to the anode 173. The power supply 175 is configured to supply a voltage V2 between the anode 173 and the cathode 171. Power supply 175 is a high voltage power supply, typically of more than 20 kV. In use, electrons 176 are accelerated towards the anode 173 due to the high voltage V2. Collision of electrons with the anode 173 causes emission of Bremsstrahlung radiation. The Bremsstrahlung radiation has a broad spectrum and includes heat and x-ray photons (x-rays) 177. A filter may be provided at the window 178 to absorb low energy photons.

FIG. 15 shows an example x-ray tube 180 which emits X-rays 187 through an end window 188. This window 188 can form a beam of radiation as shown by 50i-50ii in the exemplary embodiment of FIG. 4. This type of x-ray tube 180 is called a transmission source. Many of the features are the same as FIG. 14 and are labelled with the same reference numerals. Operation of this tube is similar to FIG. 14 and one of the main differences is described. The x-ray tube 180 has a cathode 171, a filament 172 and an anode 183. The anode 183 forms an end window in housing 189 of the x-ray tube, or the anode 183 can be positioned adjacent to an end window of the housing of the x-ray tube. A filter may be provided at the window 188 to absorb low energy photons. One advantage of this type of x-ray tube is improved heat dissipation as the anode 183 is now part of, or nearer to, the external surface of the housing and is not contained within the housing 189. The x-ray tubes 170, 180 comprise a housing or chamber 179, 189 which is typically formed of metal or glass. The housing 179, 189 is evacuated, i.e. the interior of the housing is a vacuum. The housing 179, 189 is shielded, apart from at the window 178, 188. The shielding reduces, or prevents, unwanted emission of radiation. In FIG. 14 the window 178 is provided on a side of the housing 179, alongside the anode 173. In FIG. 15 the window 188 is provided at an end of the housing 189, and x-rays are emitted from the anode 183 through the end window.

Figure 16:
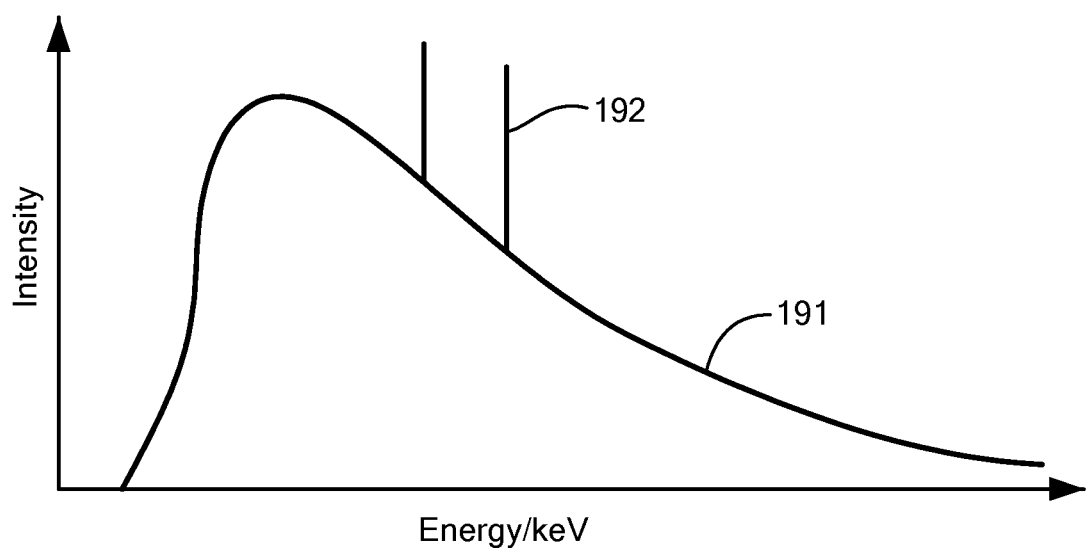
FIG. 16 shows an example graph of X-ray emissions from an X-ray tube according to one non-limiting embodiment.

FIG. 16 shows a graph of Bremsstrahlung radiation output by the x-ray tubes 170, 180. The vertical axis represents intensity, or number of photons. The horizontal axis represents energy per photon. The graph has a general curved shape 191, and may include one or more peaks 192 at particular energy values. Energy at low values may be removed by the filter at the window. Increasing the voltage V2 between the anode 173, 183 and the cathode 171 increases the energy of electrons 176 striking the anode 173, 183 and increases 15 number of higher-energy x-ray photons. This has the effect of widening the graph of FIG. 16. Increasing the voltage V1 across the filament 172 (i.e. the tube current 11) increases the rate of thermionic emission and the flow of electrons towards the anode and increases the number of x-ray photons generated at the anode. This increases the intensity (y-axis), but the overall shape of the graph remains the same.

The total dose of x-ray radiation delivered to a sample depends on: x-ray tube current (11) which controls a number of x-ray photons emitted; x-ray tube voltage (V2) which controls energy of emitted x-ray photons; and time for which radiation is emitted, i.e. the irradiation cycle.

The irradiation system of the invention can comprise a single x-ray tube 120. Each x-ray tube can be of the type shown in FIG. 14 or 15. The x-ray tubes can be positioned at a required position within the shielded housing to form the selected beam or irradiation and irradiation volume. It will be understood that a single power supply can be provided to generate V1 and V2.

The power supply can independently control the voltage(s) applied to the cathodes, anodes and filaments to independently control X-ray radiation output by the radiation source.

The irradiation system can comprise a single radiation source for imaging and for irradiation. In use, the irradiation system can first use the radiation source and imaging control technology including a radiation detector to acquire imaging data about one or more samples. The radiation source can be controlled to operate at a low radiation level. The irradiation system can then use the same radiation source to irradiate the one or more samples at a comparatively higher radiation level. The rate of the rotating mechanism and/or the orientation of the rotating canister relative to the radiation source can be selectively controlled to move the samples into, or through, the irradiation volume while the imaging is performed. Informed by the imaging data, the rate of rotation of the rotating mechanism or orientation of the rotating canister relative to the radiation source can then be selectively controlled to move the samples into, or through, the irradiation volume while the irradiation is performed.

Figure 17A:
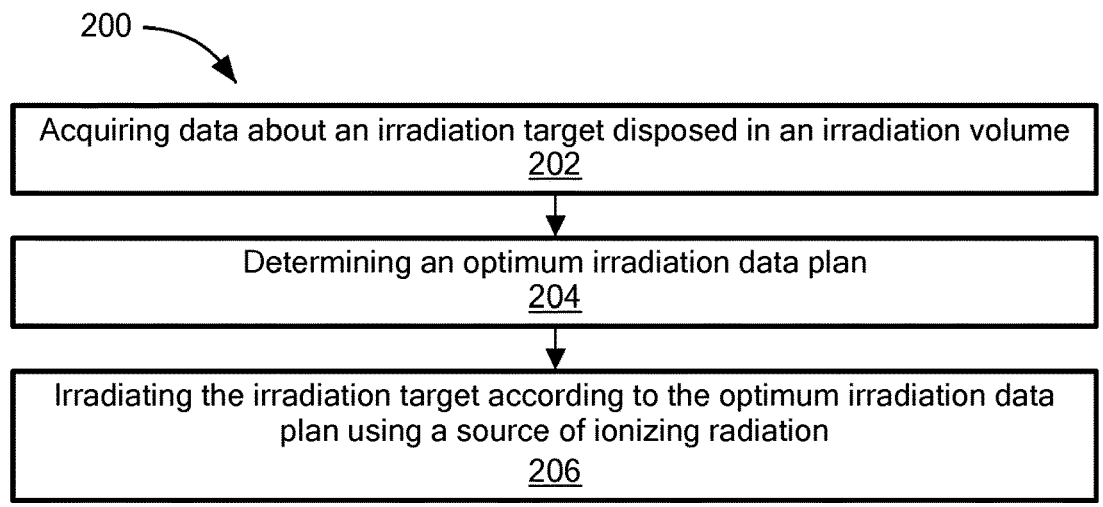
FIG. 17A shows a schematic corresponding to a method of operating the irradiation system according to one non-limiting embodiment.

FIG. 17A shows a method 200 of operating the irradiation system. The first step includes the step of acquiring data about an irradiation target corresponding to a material for irradiation disposed in an irradiation volume, as shown by step 202. The second step includes determining an optimum irradiation data plan, as shown by step 204. The third step includes irradiating the irradiation target according to the optimum irradiation data plan using a source of ionizing radiation, as shown by step 206.

The irradiation data plan includes one or more of the following parameters:
- a total radiation dose (gray or Gy corresponding to the absorption of one joule of radiation energy per kilogram of matter);
- a rate of radiation delivery (rem (roentgen equivalent man) or millirem ($1/1000^{th}$ of a rem) per unit time typically measured in minutes or hours) including whether said rate of radiation delivery is fixed, or varying over a total duration of the irradiation cycle;
- a total duration of the irradiation (typically measured in minutes or hours);
- a radiation output by an activated radiation source including whether said output is fixed, or varying over a total duration of the irradiation cycle, where radiation output is determined by (i) tube current to control energy per photon and (ii) tube voltage V2 to control energy per photon;
- a beam angle of the activated radiation including whether said beam angle is fixed or varying over total duration of irradiation cycle. As described above, beam angle can be controlled by a collimator.

Figure 17B:
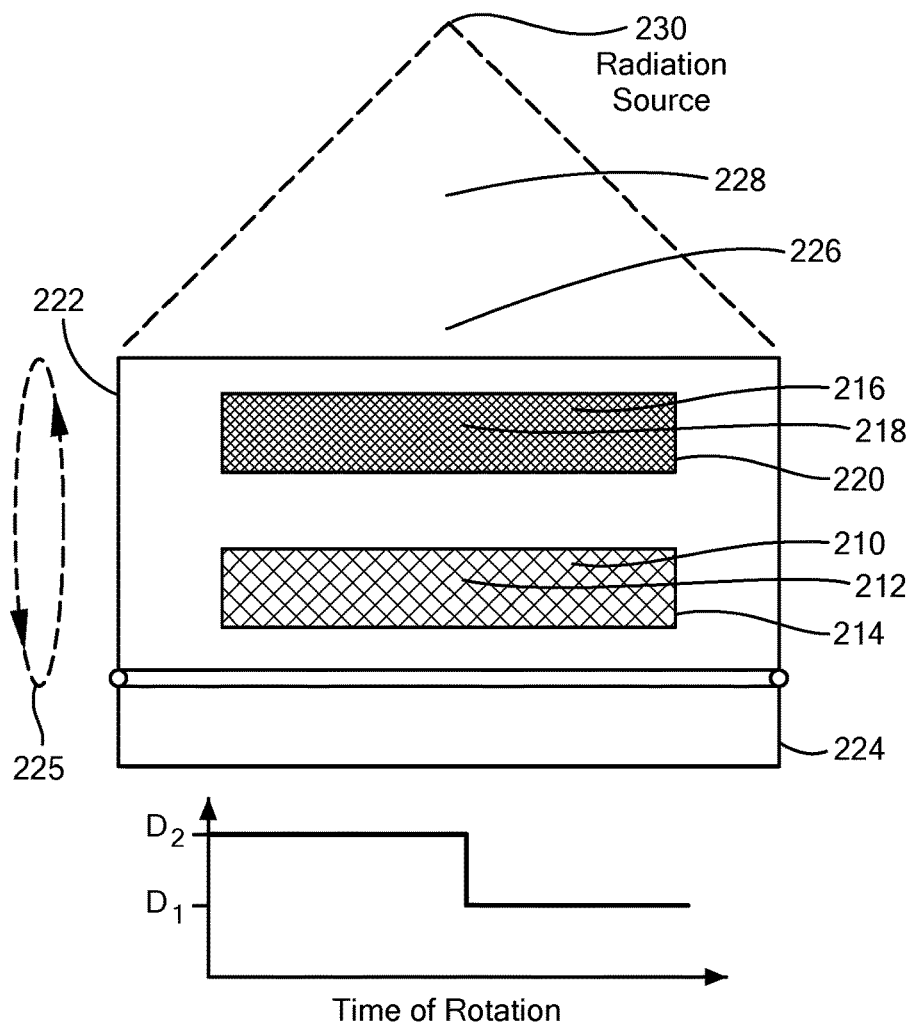
FIG. 17B shows a side cut away view of a canister disposed in a field of a radiation beam emitted from a radiation source and a graph showing an example of varying dose during irradiation according to one non-limiting embodiment.

For example, data from the control technology such as control image data can indicate that one of the samples has a higher density, or a higher density region, and therefore requires a higher energy of radiation. FIG. 17B is a schematic representation showing a first sample 210 having a first region 212 contained in a first containment device 214 and a second sample 216 having a comparatively more dense second region 218 contained with a second containment device 220 where each of the first and second samples are stacked in a canister 222. At the rotating stage or auto roll mechanism 224 rotates the canister 222 in the direction shown by arrow 225, each of first region 212 and second region 218 moves into and away from the portion 226 of the irradiation volume 228 which is closer to the radiation source 230. The irradiation data plan can incorporate increasing radiation level of the radiation source 230 when the higher density sample is nearest the radiation source 230. For example, tube voltage (energy per photon) can be increased when a denser sample (or a denser region of a sample) is nearer to the radiation source. Tube voltage can be decreased when the lower density sample is closer to the radiation source. The lower part of FIG. 17B shows the radiation level delivered by the radiation source 230 over a period of time. The radiation level begins at a value D2 when the denser second region 218 of the sample passes through the portion 226 of the irradiation volume 228 which is closer to the radiation source 230. The radiation level decreases to a value of D1 when the canister rotates and the less dense region 214 of the sample passes through the portion 226 of the irradiation volume 228 which is closer to the radiation source 230. This is a relatively simple example. The radiation profile can have a more complicated shape. The shape of the beam can be varied to focus radiation towards or in a particular region of the sample. The same method can be applied to an entire sample, so that a first sample is irradiated at a first radiation level and a second sample is irradiated at a second radiation level.

Further, in some non-limiting embodiments, the method can include compensation for the amount of radiation absorbed by packaging including the canister and/or containment device. The estimated amount of radiation absorbed by the packaging can be considered and added to the desired dose to be provided to the sample in order to fine tune the amount of radiation to which the sample and packaging should be subject in order to achieve the desired dose to the sample. It is to be understood that this method may be automated in some non-limiting embodiments in order to reduce user workload in calculating the required dose to be applied to the irradiation volume in which the packaged sample is provided.

FIG. 17C is a schematic illustration of an image acquired by the irradiation system 10 in which a sample 138 is contained within packaging 138$p$ including a canister. In other non-limiting examples, the packaging 138$p$ includes a canister and an optional containment device within the canister containing the sample. A first region R1 of the image corresponds to the region of the irradiation volume where X-ray radiation which has passed through sample packaging 138$p$ but has not passed through any portion of the sample 138 (a small amount of radiation may contribute to the image due to scattering by e.g. the sample 338 or portions of the system 10). A suitable second region R2 of the image corresponds to a region of the irradiation volume where X-ray radiation which has passed substantially directly from the X-ray source to the detector without passing through the sample 338 or sample packaging 338$p$ is detected.

In one non-limiting embodiment, the schematic of FIG. 17D shows the method 200 previously shown in FIG. 17A incorporating steps for estimating an amount of radiation absorbed by the packaging and adjusting or modifying the optimum irradiation data plan accordingly. The method step 202 of acquiring data about an irradiation target disposed in an irradiation volume of method 200 thus includes:

identifying a first region R1 of an image of the irradiation volume corresponding to a region in which the radiation which has passed through packaging without passing through the sample is detected (step 202$a$);

identifying a second region R2 of the image of the irradiation volume corresponding to a region in which radiation which has passed directly to the detector is detected without passing through the packaging and the sample (step 202$b$); and comparing image data of the first region R1 and second region R2 to estimate an amount of radiation absorbed by packaging (step 202$c$).

The method step of 204 thus includes step 204$a$ including determining an optimum irradiation plan including compensating for absorption of radiation by packaging.

In non-limiting embodiments, absorption of radiation by the rotating mechanism and/or shelf is similarly compensated for. Such compensation is achieved by estimating the amount of radiation absorbed by the rotating mechanism and/or shelf by the following steps:

(a) identifying a portion of an image of the irradiation volume corresponding to a region in which the radiation which has passed through the rotating mechanism and/or shelf and the packaging without passing through the sample is detected; and (b) identifying a portion of the image of the irradiation volume corresponding to a region in which radiation which has passed directly to the detector without passing through the rotating mechanism and/or shelf, the packaging and the sample is detected.

The method steps 202$a$-202$c$ can be adjusted such that the first region of the image corresponds to a portion of the irradiation volume corresponding to a region in which radiation which has passed through the rotating mechanism and/or shelf and packaging without passing through the sample is detected, and the second region of the image corresponds to a portion of the irradiation volume corresponding to a region in which radiation which has passed directly to the detector without passing through the rotating mechanism and/or shelf, the packaging, and the sample is detected. The method step 204$a$ can thus include determining an optimum irradiation plan to achieve a desired irradiation of a sample by adjusting the optimum irradiation plan to compensate for absorption of radiation by packaging, the rotating mechanism and/or the shelf.

The radiation dose used during imaging is typically lower, or much lower, than the radiation dose used during irradiation. Radiation dose is measured using the SI unit Gray (Gy). Imaging typically uses a dose of 0.005-0.1 Gy. Irradiation typically uses a dose of at least 1 Gy but some applications can use a lower dose, such as a dose of at least 0.02 Gy. In contrast, imaging is typically in the range of 0.001-0.1 Gy.

Properties of samples transported into the irradiation system can: (i) vary within one of the samples (e.g. a large bale with a damp central portion and drier outer portions, or a bale with denser region): (ii) vary from sample to sample; or (iii) be uniform (or assumed to be uniform) across a batch of samples, e.g. human plasma. The imaging and determining optimum use steps (steps 202, 204) can be performed on a per sample basis, or on a less frequent basis. When performed on a less frequent basis, data from an earlier imaging operation can be used until new data is obtained. It is also possible to define one or more templates of parameter values for particular samples or conditions.

The controller can vary a speed of the rotation mechanism. Varying the speed of the rotation mechanism varies speed of movement of a sample through the irradiation volume. Reducing the speed increases the length of time that the sample remains in the irradiation volume. Increasing the speed reduces the length of time that the sample remains in the irradiation volume. Varying the energy level and speed can vary the radiation dose delivered to the sample (or region of the sample).

In a simpler example, where the irradiation lacks a radiation detector and/or a capability to image the irradiation volume, the irradiation system can receive inputs to set parameters for an irradiation cycle such as: a total radiation dose; a rate of delivering radiation; a total duration of the irradiation; power of the radiation source; a beam angle of the radiation. The irradiation apparatus can determine operating parameters for the radiation source based on the input values.

The optimum imaging data plan can also be modified, adjusted and/or optimized based upon a comparison between an initial microbial contamination of the pre-irradiated product material or sample for irradiation and the corresponding microbial contamination regulatory standards for a target jurisdiction where the sample will be distributed, sold or otherwise marketed. A schematic of such a method 400 is shown by the non-limiting embodiment shown in FIG. 18. The method 400 includes determining initial or pre-irradiation microbial contamination data by weight and/or by volume for each of one or more selected microbes in a sample for irradiation (step 402); determining data including a weight and/or a volume of the sample for irradiation (step 404); calculating an initial or pre-irradiation microbial contamination level for each of the one or more selected microbes in the sample for irradiation (step 406); acquiring corresponding microbial contamination regulatory standards in a target jurisdiction for each of the one or more selected microbes (step 408); comparing the initial or pre-irradiation microbial contamination level for each of the one or more selected microbes in the sample for irradiation with the corresponding microbial contamination regulatory standards for the target jurisdiction for each of the one or more selected microbes (step 410); determining an optimum irradiation data plan based upon the comparison (step 412); and irradiating the sample for irradiation according to the optimal irradiation data plan using a source of ionizing radiation (414).

Figure 18:
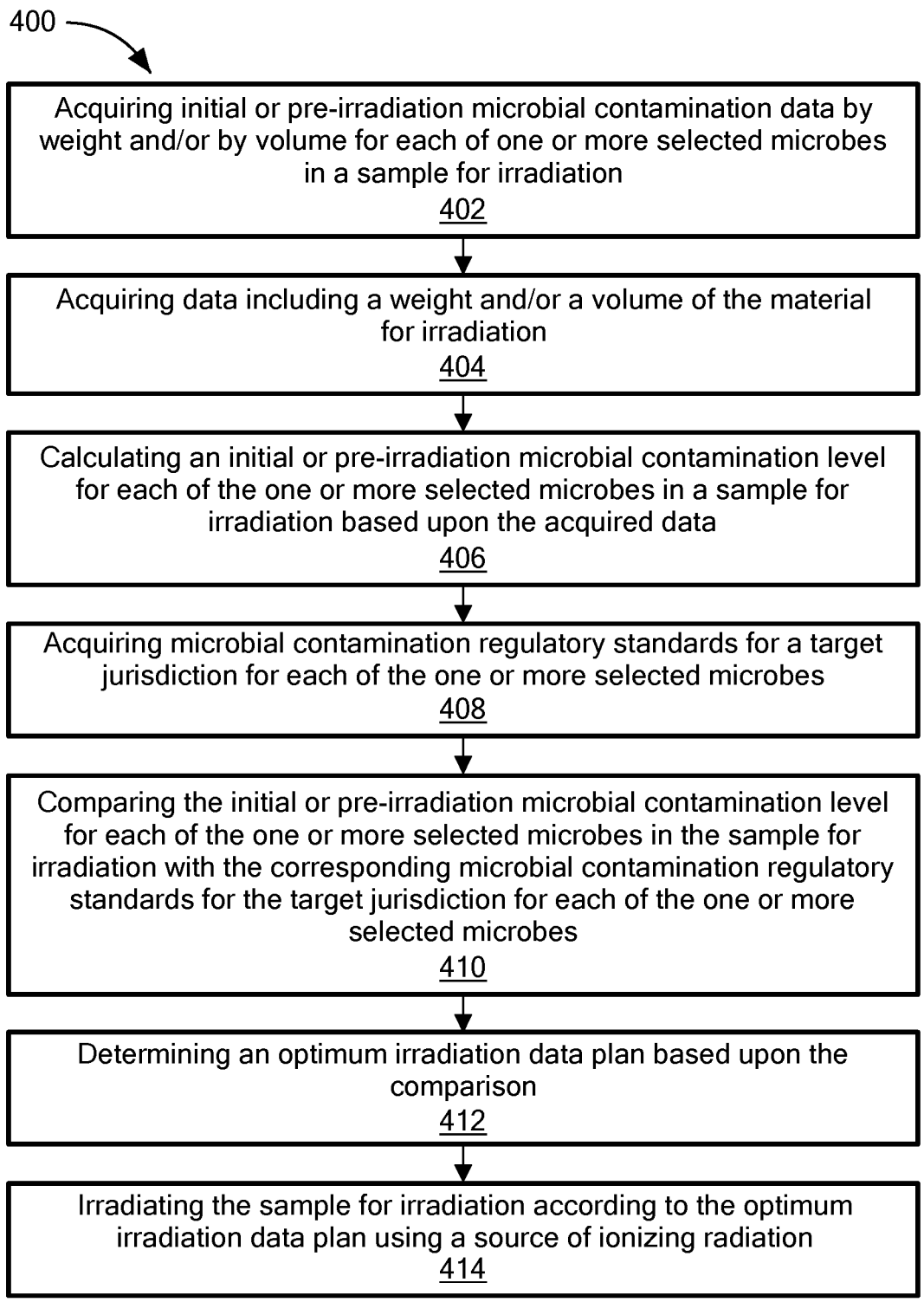
FIG. 18 shows a schematic corresponding to a method of operating the irradiation system according to one non-limiting embodiment.

In other non-limiting embodiments, steps corresponding to steps 402-410 are conducted prior to step 202 as shown in FIG. 17A or prior to steps 202a-202c as shown in FIG. 17D, where the irradiation target as described in FIG. 7A and FIG. 7D corresponds to the sample for irradiation as described in FIG. 18. In such embodiments, the steps of determining an optimum irradiation data plan (step 204, FIG. 17) or determining an optimum irradiation plan including compensating for absorption of radiation by packaging (step 204a, FIG. 17D) or by packaging, the rotating mechanism and/or the shelf, also includes determining an optimum irradiation plan including comparing the initial or pre-irradiation microbial contamination level for each of the one or more selected microbes in the sample for irradiation (corresponding to the irradiation target) with the corresponding microbial contamination regulatory standards for the target jurisdiction for each of the one or more selected microbes.

Figure 19:
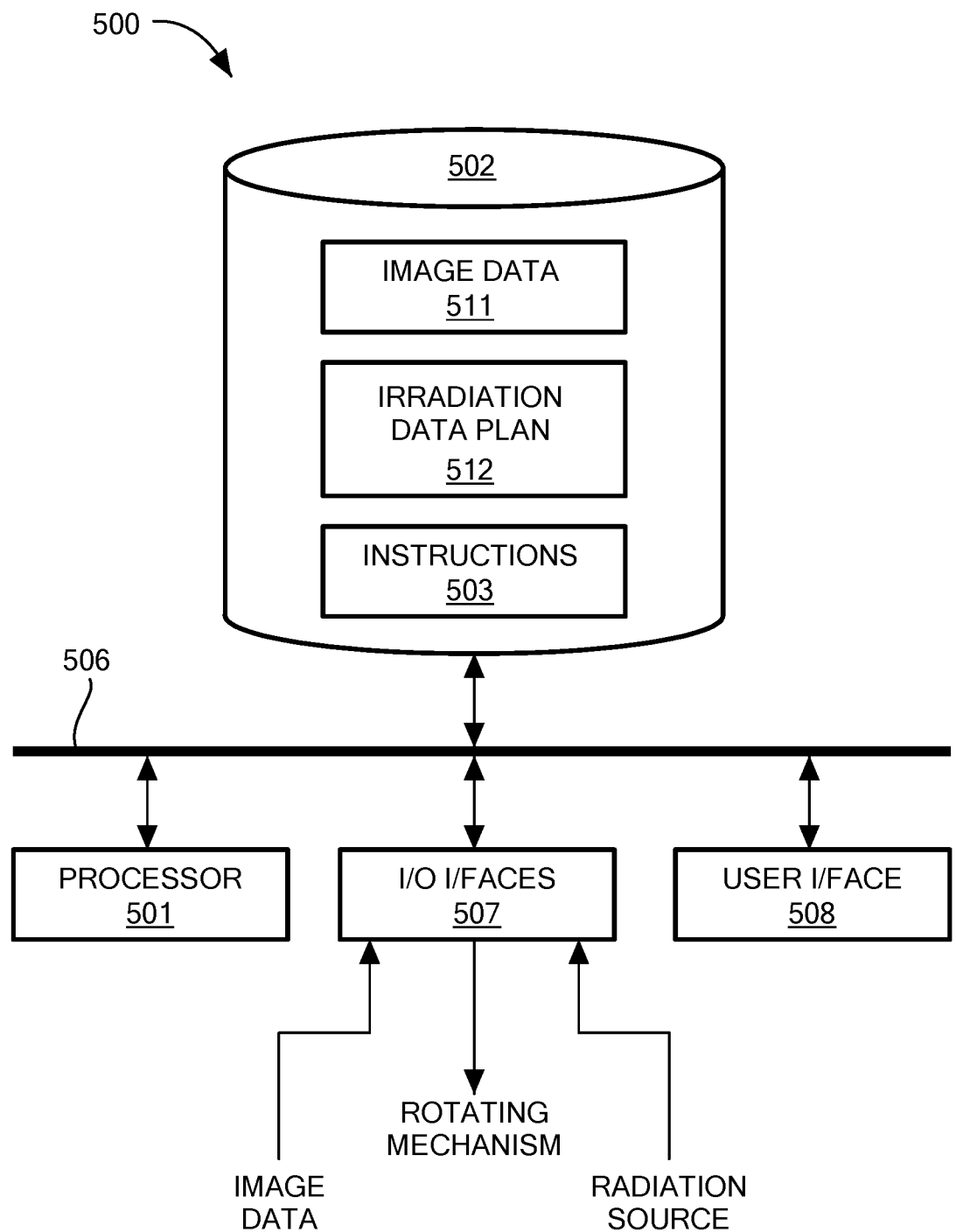
FIG. 19 shows a processing apparatus for the irradiation system according to one non-limiting embodiment.

Parameters can be input to the processing apparatus via the user interface or through the other components or components or elements of the irradiation system. FIG. 19 shows an example of a processing apparatus 500 which can implement at least part of the processing of the system. The processing apparatus 500 can implement the methods of FIG. 17A, FIG. 17D and/or FIG. 18. Processing apparatus 500 comprises one or more processors 501 which may be any type of processor for executing instructions to control the operation of the device. The processor 501 is connected to other components of the device via one or more buses 506. Processor-executable instructions 503 may be provided using any data storage device or computer-readable media, such as memory 502. The processor-executable instructions 503 comprise instructions for implementing the functionality of the described methods. The memory 502 is of any suitable type such as non-volatile memory, a magnetic or optical storage device. The processing apparatus 500 comprises input/output (I/O) interfaces 507. The I/O interfaces 507 can receive signals from the detectors and output signals to control the irradiation apparatus, e.g. power, beam width; control operation of the rotation mechanism and/or shelf positioning. The processing apparatus 500 connects to a user interface 508 which corresponds to the user interface shown by element 16 in FIG. 1. Memory 502, or a separate memory, stores data used by the processor. This can include one or more of: image data 511; and the irradiation data plan 512.

The dose may vary according to a type of application. Radiation dose is measured using the SI unit Gray (Gy) and dose rate in Gray/minute (Gy/min). Sterilization typically requires a high or a very high dose (e.g. 15-50 Gy dose for blood bags; 400-15,000 Gy dose for fruits, vegetables, nuts, meat, fish, poultry and animal feed; 2,500-15,000 Gy dose for cannabis bags/bottles). This can be delivered at a high dose rate, and may require an irradiation cycle of the order of hours, or tens of hours. Other applications can require a smaller dose, e.g. irradiation of cells for clinical research requires a dose of 0.2-25 Gy at a dose rate of 2-15 Gy/min.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

In the present specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. The contents of all references, pending patent applications and published patents, cited throughout this application are hereby expressly incorporated by reference as if set forth herein in their entirety, except where terminology is not consistent with the definitions herein. Although specific terms are employed, they are used as in the art unless otherwise indicated.

What is claimed is:

1. An irradiation system comprising:
a shielded housing;
at least one canister disposed within the shielded housing, the at least one canister containing a material for irradiation within an interior volume of the at least one canister;
wherein the at least one canister has a body disposed between a first end cap disposed at a first end of the canister and a second end cap disposed at a second end of the canister opposed to the first end;
an ionizing radiation source disposed within the shielded housing adapted for emitting an ionizing radiation having at least one selected incident irradiation field geometry directed generally at the body of the at least one canister;
wherein the at least one canister is disposed on a rotating mechanism for rotating the at least one canister about a central horizontal or longitudinal axis extending from an isocenter of the first end cap to an isocenter of the second end cap for increasing uniform distribution of radiation of the material contained within the canister;
wherein at least one of the first end cap and the second end cap includes a component configured for selectively constraining geometrically within an interior volume of the canister at least one of the material for irradiation and a containment device containing the material for irradiation for optimizing alignment to the at least one selected incident irradiation field geometry.

2. The irradiation system of claim 1 wherein at least one of the first end cap and the second end cap is configured for selectively sealing and unsealing at least a portion of a corresponding end of the canister.

3. The irradiation system of claim 1, wherein at least one of the first end cap and the second end cap has at least one port configured for fluidically connecting an exterior of the canister to an interior volume of the canister.

4. The irradiation system of claim 3, wherein the irradiation system comprises at least one channel tube having dimensions for insertion into the at least one port for fluidically connecting the exterior of the canister to the interior volume of the canister.

5. The irradiation system of claim 4, wherein at least one of the at least one port and the at least one channel tube is configured such that at least one of the at least one port and the at least one channel tube are selectively sealed and unsealed.

6. The irradiation system of claim 1, wherein the rotating mechanism is modulated or adjusted in a manner selected from the group consisting of a continuous manner, a non-continuous manner and a combination of each of the aforementioned.

7. The irradiation system of claim 1, wherein at least one of the ionizing radiation source and the rotating mechanism is controlled based on a control technology selected from the group consisting of an imaging control technology, an optical control technology, an electromagnetic closed-loop control technology, an electromagnetic semi-closed loop control technology, and at least two of the aforementioned control technologies.

8. The irradiation system of claim 1 further comprising:
a control technology including an imaging control technology having at least one radiation detector for measuring at least one of a density and a distribution of the material during irradiation based on one or more projection images through the material;
wherein the rotating mechanism is configured with at least one clearance portion for the at least one radiation detector.

9. The irradiation system of claim 1, wherein the component has an accordion-like shape which is configured for selectively folding and moving toward or folding and moving away from the interior volume of the canister thereby optimizing the interior volume of canister which falls within the selected irradiation field geometry.

10. The irradiation system of claim 1, wherein the component is configured for selective extension and contraction.

11. The irradiation system of claim 1, wherein the component is configured for selectively constraining geometrically at least one of the material for irradiation and a containment device containing the material for irradiation within the canister for minimizing movement during rotation of the canister of the at least one of the material for irradiation and the containment device containing the material for irradiation.

12. The irradiation system of claim 1, wherein the ionizing radiation source consists of one ionizing radiation source.

13. The irradiation system of claim 1 further comprising a programmable shelf on which the rotating mechanisms are disposed;
wherein the programmable shelf is selectively positioned with respect to the ionizing radiation source for achieving the at least one selected incident irradiation field geometry directed generally at the body of the at least one canister.

14. The irradiation system of claim 4 further comprising a probe configured for selective insertion of a first end of the probe to a selected position within the interior volume of the canister via at least one of the at least one port and the at least one channel tube and for selected retraction therefrom;
wherein the probe is configured for measurement of a property including at least one of a temperature level, a humidity level, and a radiation level.

15. The irradiation system of claim 1 further comprising a controller configured with a capability to integrate information received from at least one of a control technology and a probe configured for insertion into the interior volume of the canister for optimization of the irradiation system with respect to controlling at least one of:
at least one operating parameter of the source of ionizing radiation,
at least one operating parameter for the component configured for selectively constraining geometrically within the canister at least one of the material and a containment device containing the material,
at least one operating parameter of the rotating mechanism, and
at least one operating parameter for selective positioning of a programmable shelf on which the rotating mechanism is disposed;
wherein optimization of the irradiation system includes maximizing uniform distribution of radiation of the material within the canister.

16. The irradiation system of claim 1 further comprising a controller;
wherein the controller is configured with a capability for acquiring data for at least one selected microbe including a pre-irradiation microbial contamination level for at least one selected microbe on a weight or volume basis and a corresponding weight or volume of the material, and calculating a pre-irradiation microbial contamination level for the at least one selected microbe in the material based on the acquired data;
wherein the controller is configured with a capability for acquiring data including an identification of a target jurisdiction and correlating the target jurisdiction with a microbial contamination or sterilization regulatory standard for the target jurisdiction for the at least one selected microbe; and
wherein the controller is configured with a capability for determining an optimum irradiation data plan for an optimization of at least one operating parameter of the source of ionizing radiation based upon a comparison of the pre-irradiation microbial contamination level for at least one selected microbe in the material and the microbial contamination or sterilization regulatory standard for the target jurisdiction for the at least one selected microbe.

17. The irradiation system of claim 16, wherein the at least one operating parameter comprises at least one of:
a total radiation dose (gray);
a rate of radiation delivery (rem) per unit time (minutes);
a total duration of an irradiation (minutes);
a radiation output by the source of ionizing radiation; and
a beam angle of the source of ionizing radiation upon activation over the duration of the irradiation.

18. The irradiation system of claim 1, wherein at least one of the operating parameters including the rate of radiation delivery, the radiation output and the beam angle comprises a manner of operation of the operating parameter over the total duration of the irradiation selected from group consisting of varying, fixed and a combination of the aforementioned.

19. A device for receiving ionizing radiation from an ionizing radiation source comprising:
a canister having a body, a first end cap disposed at a first end of the body and a second end cap disposed at a second end of the body opposed to the first end;
wherein at least one of the first end cap and the second end cap has a component which is configured for selective extension and contraction for selectively constraining geometrically within the canister at least one of a material for irradiation contained within an interior volume of the canister and a containment device containing the material for irradiation within the interior volume of the canister for optimizing alignment to at least one selected incident irradiation field geometry directed generally at the body of the canister from the ionizing radiation source.

20. A method of irradiation of a material comprising:
providing an ionizing radiation source within a shielded housing;
providing at least one canister disposed on a rotating mechanism within the shielded housing;
wherein the at least one canister contains a material for irradiation within an interior volume of the at least one canister;
wherein the at least one canister has a body disposed between a first end cap disposed at a first end of the canister and a second end cap disposed at a second end of the canister opposed to the first end;
emitting an ionizing radiation having at least one selected incident irradiation field geometry directed generally at the body of the at least one canister from the ionizing radiation source;
rotating the at least one canister about a central horizontal or longitudinal axis extending from a first isocenter of the first end cap to a second isocenter of the second end cap for increasing uniform distribution of radiation of the material contained within the canister; and
providing a component for selectively constraining geometrically within the canister at least one of the material for irradiation and a containment device containing the material for irradiation for optimizing alignment of the material for irradiation to a geometry of the beam of radiation incident on the body of the canister.

21. The irradiation system of claim 16,
wherein the controller is configured with a capability for acquiring data for the at least one selected microbe including the pre-irradiation microbial contamination level for the at least one selected microbe on a weight or volume basis and the corresponding weight or volume of the material based on at least one of manual data input via a user interface integrated with the controller, data input received by the controller via a weighing mechanism integrated with the controller, data input received by the controller via a scanning of a machine readable information code, and a combination of the aforementioned.

22. An irradiation system comprising:
a shielded housing;
at least one canister disposed within the shielded housing, the at least one canister containing a material for irradiation within an interior volume of the at least one canister;
wherein the at least one canister has a body disposed between a first end cap disposed at a first end of the canister and a second end cap disposed at a second end of the canister opposed to the first end; and
an ionizing radiation source disposed within the shielded housing adapted for emitting an ionizing radiation having at least one selected incident irradiation field geometry directed generally at the body of the at least one canister;
wherein the at least one canister is disposed on a rotating mechanism for rotating the at least one canister about a central horizontal or longitudinal axis extending from an isocenter of the first end cap to an isocenter of the second end cap for increasing uniform distribution of radiation of the material contained within the canister; and
wherein at least one of the first end cap and the second end cap has at least one port configured for fluidically connecting an exterior of the canister to an interior volume of the canister.

23. The irradiation system of claim 22, wherein the irradiation system comprises at least one channel tube having dimensions for insertion into the at least one port for fluidically connecting the exterior of the canister to the interior volume of the canister.

24. The irradiation system of claim 23, wherein at least one of the at least one port and the at least one channel tube is configured such that at least one of the at least one port and the at least one channel tube are selectively sealed and unsealed.

25. An irradiation system comprising:
a shielded housing;
at least one canister disposed within the shielded housing, the at least one canister containing a material for irradiation within an interior volume of the at least one canister;
wherein the at least one canister has a body disposed between a first end cap disposed at a first end of the canister and a second end cap disposed at a second end of the canister opposed to the first end;
an ionizing radiation source disposed within the shielded housing adapted for emitting an ionizing radiation having at least one selected incident irradiation field geometry directed generally at the body of the at least one canister;
wherein the at least one canister is disposed on a rotating mechanism for rotating the at least one canister about a central horizontal or longitudinal axis extending from an isocenter of the first end cap to an isocenter of the second end cap for increasing uniform distribution of radiation of the material contained within the canister; and
a control technology including an imaging control technology having at least one radiation detector for measuring at least one of a density and a distribution of the material during irradiation based on one or more projection images through the material;
wherein the rotating mechanism is configured with at least one clearance portion for the at least one radiation detector.

26. An irradiation system comprising:
a shielded housing;
at least one canister disposed within the shielded housing, the at least one canister containing a material for irradiation within an interior volume of the at least one canister;

wherein the at least one canister has a body disposed between a first end cap disposed at a first end of the canister and a second end cap disposed at a second end of the canister opposed to the first end;
an ionizing radiation source disposed within the shielded housing adapted for emitting an ionizing radiation having at least one selected incident irradiation field geometry directed generally at the body of the at least one canister;
wherein the at least one canister is disposed on a rotating mechanism for rotating the at least one canister about a central horizontal or longitudinal axis extending from an isocenter of the first end cap to an isocenter of the second end cap for increasing uniform distribution of radiation of the material contained within the canister; and
a probe configured for selective insertion of a first end of the probe to a selected position within the interior volume of the canister via at least one of the at least one port and the at least one channel tube and for selected retraction therefrom;
wherein the probe is configured for measurement of a property including at least one of a temperature level, a humidity level, and a radiation level.

27. An irradiation system comprising:
a shielded housing;
at least one canister disposed within the shielded housing, the at least one canister containing a material for irradiation within an interior volume of the at least one canister;
wherein the at least one canister has a body disposed between a first end cap disposed at a first end of the canister and a second end cap disposed at a second end of the canister opposed to the first end;
an ionizing radiation source disposed within the shielded housing adapted for emitting an ionizing radiation having at least one selected incident irradiation field geometry directed generally at the body of the at least one canister;
wherein the at least one canister is disposed on a rotating mechanism for rotating the at least one canister about a central horizontal or longitudinal axis extending from an isocenter of the first end cap to an isocenter of the second end cap for increasing uniform distribution of radiation of the material contained within the canister; and
a controller configured with a capability to integrate information received from at least one of a control technology and a probe configured for insertion into the interior volume of the canister for optimization of the irradiation system with respect to controlling at least one of:
at least one operating parameter of the source of ionizing radiation,
at least one operating parameter for at least one component configured for selectively constraining geometrically within the canister at least one of the material and a containment device containing the material,
at least one operating parameter of the rotating mechanism, and
at least one operating parameter for selective positioning of a programmable shelf on which the rotating mechanism is disposed;
wherein optimization of the irradiation system includes maximizing uniform distribution of radiation of the material within the canister.

28. An irradiation system comprising:
a shielded housing;
at least one canister disposed within the shielded housing, the at least one canister containing a material for irradiation within an interior volume of the at least one canister;
wherein the at least one canister has a body disposed between a first end cap disposed at a first end of the canister and a second end cap disposed at a second end of the canister opposed to the first end;
an ionizing radiation source disposed within the shielded housing adapted for emitting an ionizing radiation having at least one selected incident irradiation field geometry directed generally at the body of the at least one canister;
wherein the at least one canister is disposed on a rotating mechanism for rotating the at least one canister about a central horizontal or longitudinal axis extending from an isocenter of the first end cap to an isocenter of the second end cap for increasing uniform distribution of radiation of the material contained within the canister;
wherein the controller is configured with a capability for acquiring data for at least one selected microbe including a pre-irradiation microbial contamination level for at least one selected microbe on a weight or volume basis and a corresponding weight or volume of the material, and calculating a pre-irradiation microbial contamination level for the at least one selected microbe in the material based on the acquired data;
wherein the controller is configured with a capability for acquiring data including an identification of a target jurisdiction and correlating the target jurisdiction with a microbial contamination or sterilization regulatory standard for the target jurisdiction for the at least one selected microbe; and
wherein the controller is configured with a capability for determining an optimum irradiation data plan for an optimization of at least one operating parameter of the source of ionizing radiation based upon a comparison of the pre-irradiation microbial contamination level for at least one selected microbe in the material and the microbial contamination or sterilization regulatory standard for the target jurisdiction for the at least one selected microbe.

29. The irradiation system of claim 28, wherein the at least one operating parameter comprises at least one of:
a total radiation dose (gray);
a rate of radiation delivery (rem) per unit time (minutes);
a total duration of an irradiation (minutes);
a radiation output by the source of ionizing radiation; and
a beam angle of the source of ionizing radiation upon activation over the duration of the irradiation.

30. The irradiation system of claim 29,
wherein the controller is configured with a capability for acquiring data for the at least one selected microbe including the pre-irradiation microbial contamination level for the at least one selected microbe on a weight or volume basis and the corresponding weight or volume of the material based on at least one of manual data input via a user interface integrated with the controller, data input received by the controller via a weighing mechanism integrated with the controller, data input received by the controller via a scanning of a machine readable information code, and a combination of the aforementioned.

* * * * *